(12) United States Patent
Wald

(10) Patent No.: US 8,815,827 B2
(45) Date of Patent: Aug. 26, 2014

(54) MYELOID DIFFERENTIATION INDUCING AGENTS

(75) Inventor: David Wald, University Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 1064 days.

(21) Appl. No.: 12/664,469

(22) PCT Filed: Jun. 12, 2008

(86) PCT No.: PCT/US2008/066700
§ 371 (c)(1),
(2), (4) Date: Jun. 25, 2010

(87) PCT Pub. No.: WO2008/154629
PCT Pub. Date: Dec. 18, 2008

(65) Prior Publication Data
US 2010/0267656 A1   Oct. 21, 2010

Related U.S. Application Data

(60) Provisional application No. 60/943,415, filed on Jun. 12, 2007.

(51) Int. Cl.
*A61K 31/70* (2006.01)
(52) U.S. Cl.
USPC .................................................. 514/45; 514/48

(58) Field of Classification Search
CPC .................................................. A61K 31/7076
USPC ...................................................... 514/45, 48
See application file for complete search history.

(56) References Cited

PUBLICATIONS

Montgomery et al., Journal of Medicinal and Pharmaceutical Chemistry, 1961, vol. 3(2), pp. 265-288.*
Sweeney et al., Cancer Research, 2003, vol. 63, pp. 1304-1310.*
Christopher A. Warlick et al., Maintenance of Differential Methotrexate Toxicity Between Cells Expressing Drug-Resistant and Wild-Type Dihydrofolate Reductase Activities in the Presence of Nucleosides through Nucleoside Transport Inhibition, 59 Biochem. Pharm. 141 (2000).*
Steward Sell, Leukemia: Stem Cells, Maturation Arrest, and Differentiation Therapy, 1 Stem Cell Revs. 197, 198 (2005).*
Gupte, et al. "6-Benzylthionosine Analogues: Promising Antitoxoplasmic Agents as Inhibitors of the Mammalian Nucleoside Transporter ENT1 (es)", Biochemical Pharmacology, 2005, vol. 71, pp. 69-73, especially p. 71, Table 1.
Honma, "Adenine Analogs as Potential Differentiation Therapy Agents for Acute Myeloid Leukemia", Drug Development Research, 2003, vol. 59, pp. 14-22, especially p. 14, Introduction; p. 15; p. 19.

* cited by examiner

*Primary Examiner* — Traviss C McIntosh, III
(74) *Attorney, Agent, or Firm* — Tarolli, Sundheim, Covell & Tummino LLP

(57) ABSTRACT

Myeloid differentiating agents can be used in the treatment of myeloid disorders.

17 Claims, 13 Drawing Sheets

A
B
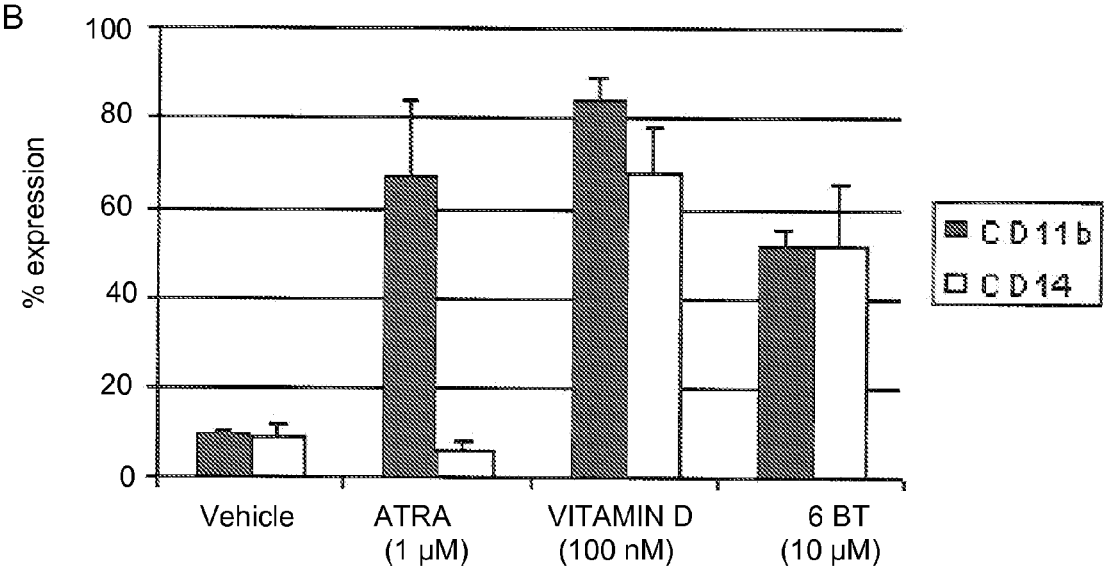
FIG. 1A-B

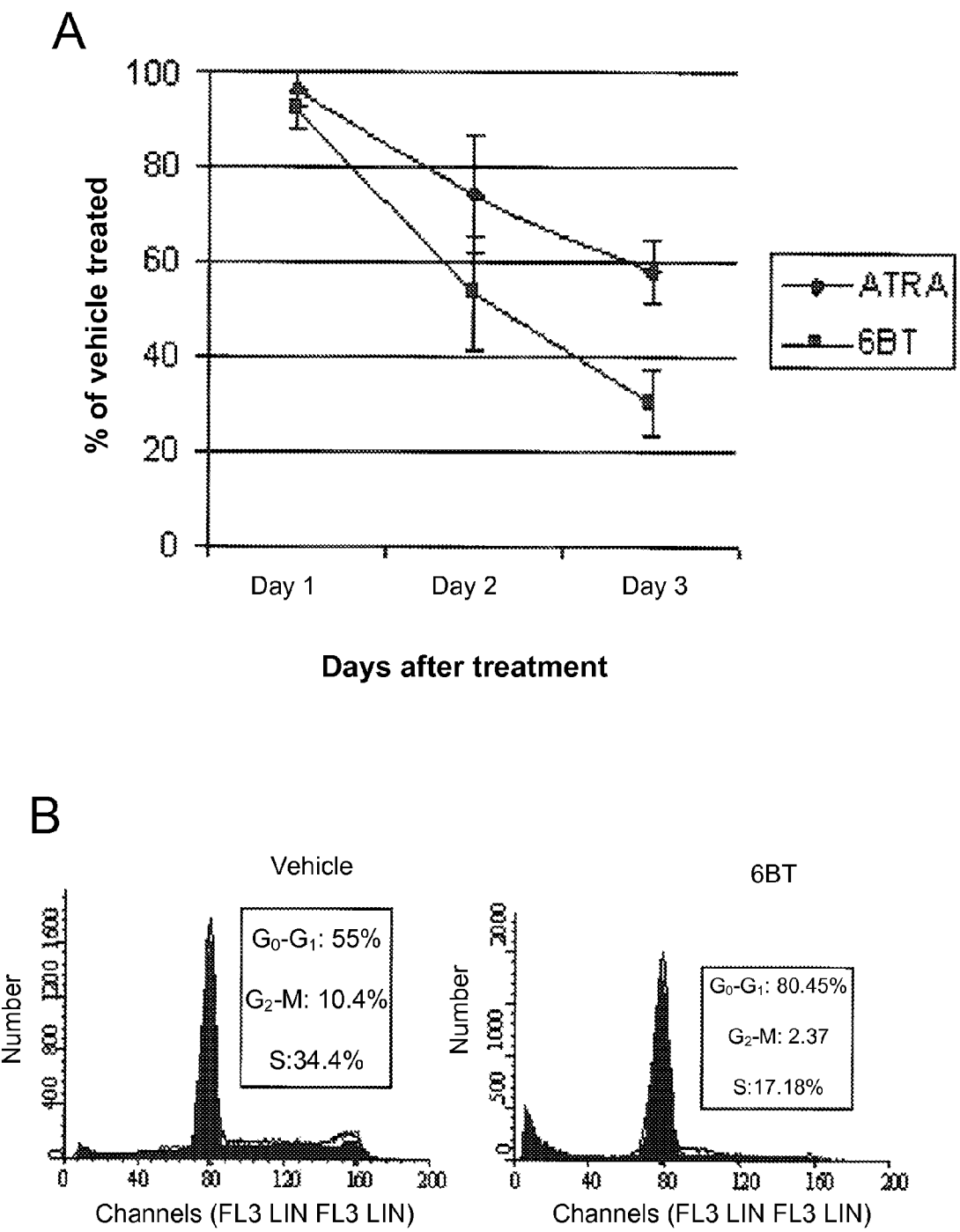
FIG. 2A-B

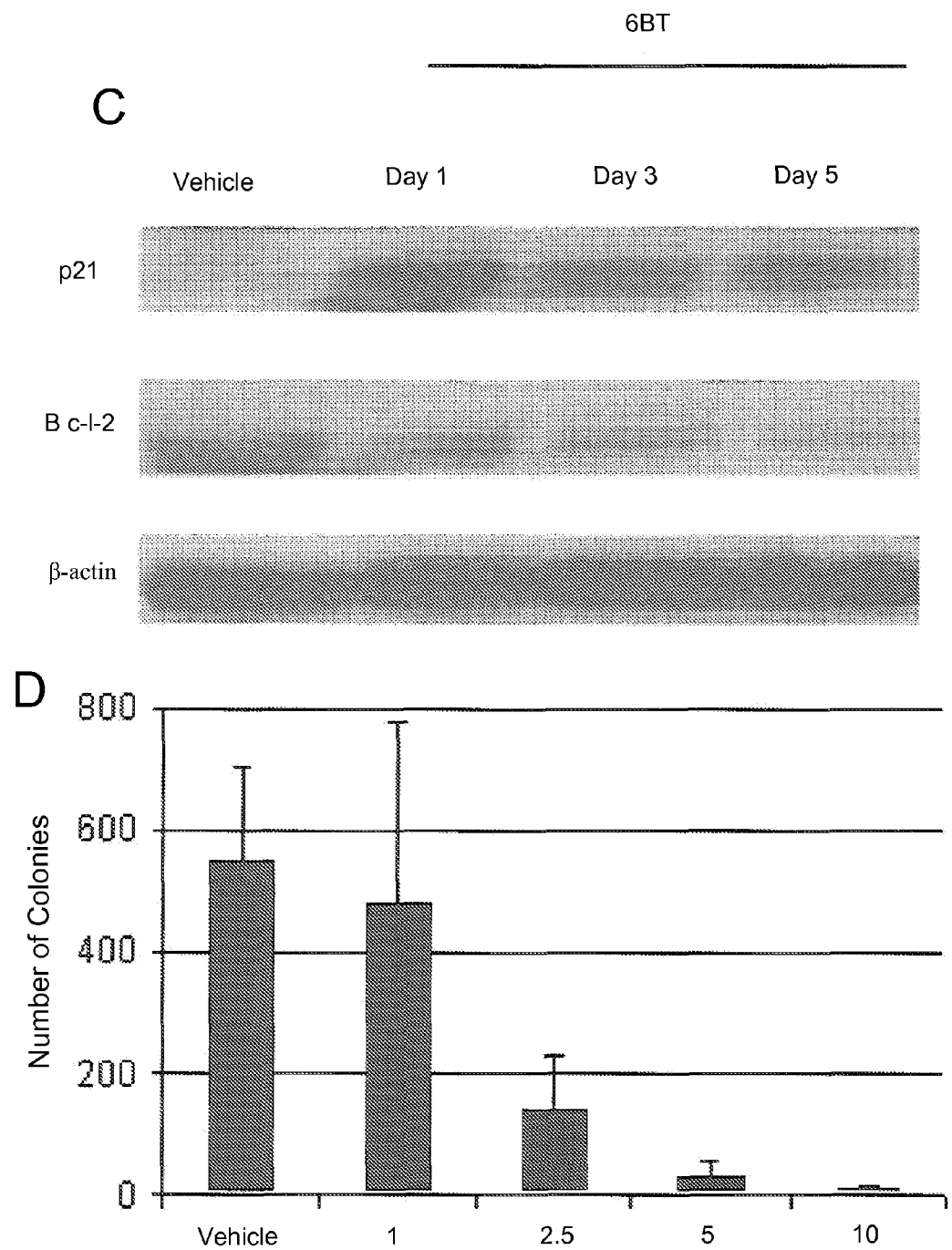
FIG. 2C-D

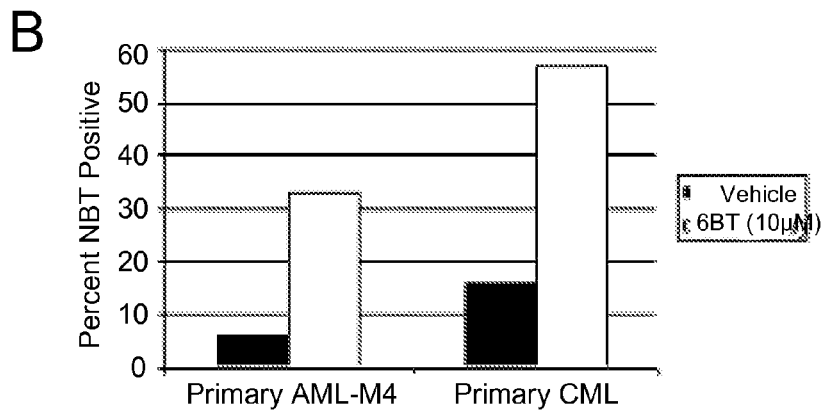
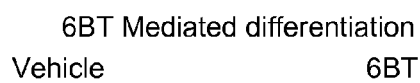
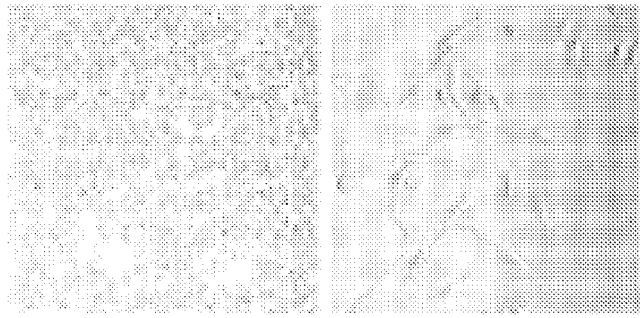
Primary AML-M4
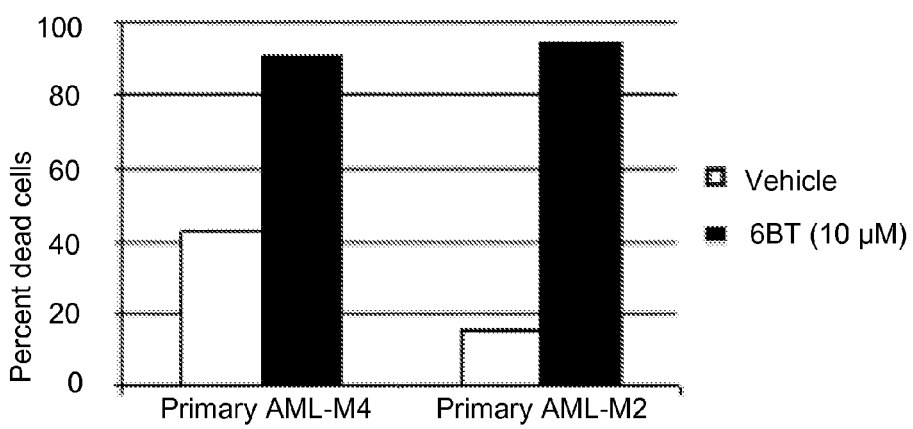
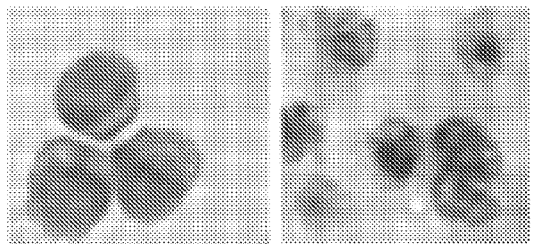
Primary AML-M2
FIG. 3B

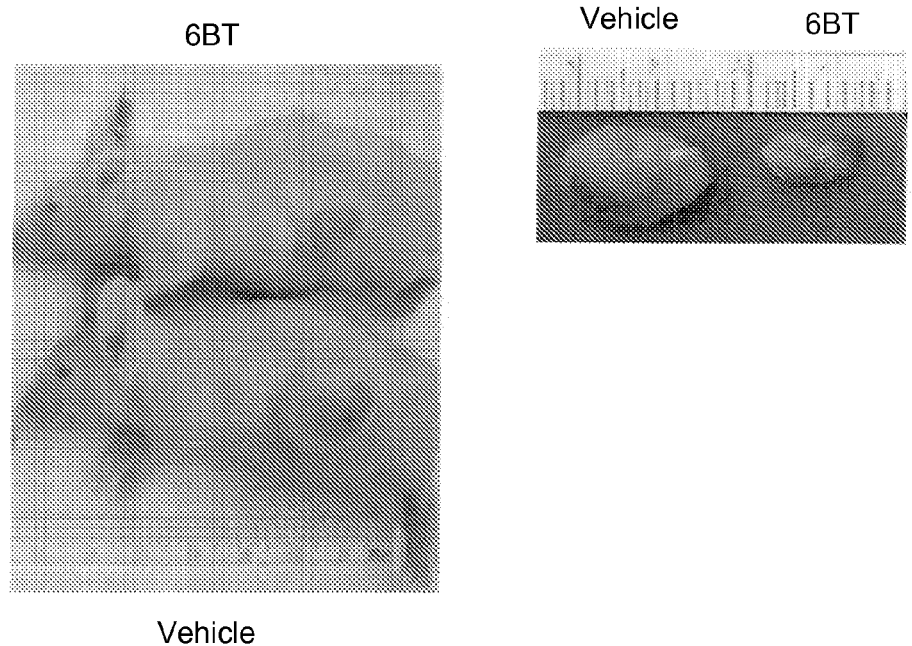
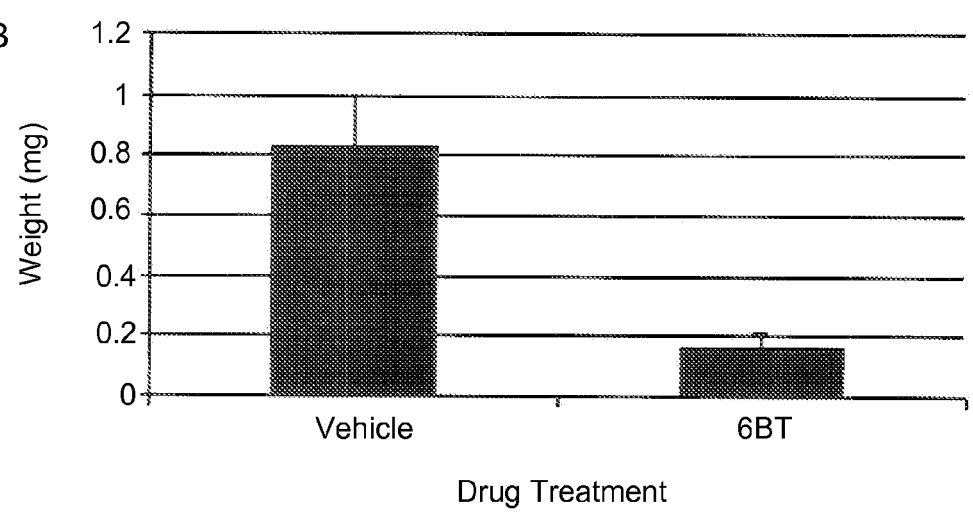
FIGS. 4A-B

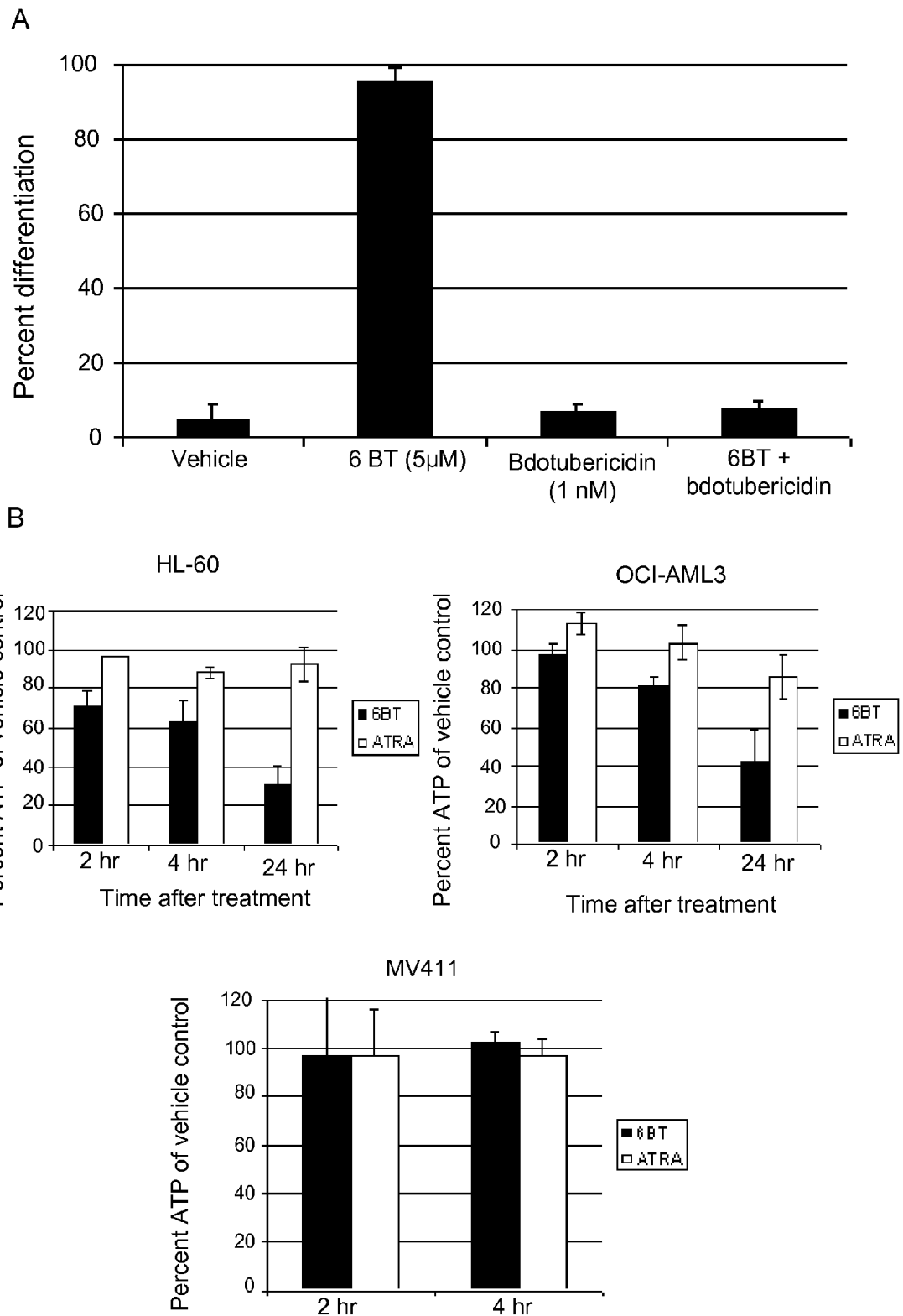
FIGS. 5A-B

MYELOID DIFFERENTIATION INDUCING AGENTS

RELATED APPLICATION

This application corresponds to PCT/US08/66700, filed Jun. 12, 2008, which claims the benefit of U.S. Provisional Application No. U.S. 60/943,415, filed Jun. 12, 2007, which is herein incorporated by reference it its entirety.

TECHNICAL FIELD

The present invention relates to compounds or therapeutic agents that can be used promote differentiation of immature myeloid cells, and more particularly to compositions and therapeutics used to treat myeloid disorders and as a myeloablative therapy.

BACKGROUND

Acute myeloid leukemia (AML) is a broad range of disorders that are all characterized by leukemic cells that have a differentiation arrest. AML can be classified morphologically according to the French-American-British criteria by the degree of differentiation as well as extent of cell maturation as M0-M7. Treatment for all subtypes of AML is very similar, except for acute promyelocytic leukemia (APL, M3 subtype). Traditional therapy involves combination systemic chemotherapy. Several different approaches are utilized; however, they usually involve an induction therapy with cytarabine and a second chemotherapeutic, such as daunorubicin or idarubicin and consolidation therapy with either a bone marrow transplant or additional chemotherapy. Besides significant side effects from the traditional chemotherapeutics, the efficacy of these agents in treating AML is poor.

To date the only exception to the poor treatment options for AML is the success of all-trans retinoic acid (ATRA) for one relatively uncommon subtype (5-10% of AML), APL. Utilizing a combination of ATRA and chemotherapy, the long-term survival and presumed cure of 75-85% of patients is possible. ATRA illustrates the great promise for new agents with greater efficacy and less toxicity. In fact, elderly patients with APL who cannot tolerate traditional chemotherapy can achieve complete remission with therapies that utilize ATRA. ATRA's success stems from the fact that AML is a clonal disease characterized by the arrest of differentiation of immature myeloid cells. ATRA overcomes this block in differentiation by forcing leukemic cells to terminally differentiate so that they are no longer capable of dividing. Unfortunately, APL is a rare subtype of AML and ATRA has not been found to be clinically useful for other subtypes.

Though many compounds have been shown to have some differentiation-inducing effects in vitro, their clinical utility has been limited by either suboptimal differentiation-inducing capacity and/or toxicity. For example, Vitamin D3 induces potent differentiation, however, it also causes severe hypercalcemia at the required dose. Treatments that promote the differentiation of immature myeloid cells hold considerable promise in improving the long term survival of AML patients while avoiding some of the toxicities of traditional chemotherapy. Treatment of leukemia could be revolutionized by novel compounds due to their potential to cure leukemia and provide elderly patients with alternative nontoxic regimens.

SUMMARY OF THE INVENTION

The present invention relates to compounds or therapeutic agents that can be used as myeloid differentiation inducing agents. More particularly, the present invention relates to myeloid differentiation inducing agents that can be used to treat myeloid disorders (e.g., acute myeloid leukemia).

In one aspect of the present invention, a method of inducing myeloid differentiation in a subject includes administering to the subject a therapeutically effective amount of at least one inosine analog myeloid differentiating agent having the following general formula (I):

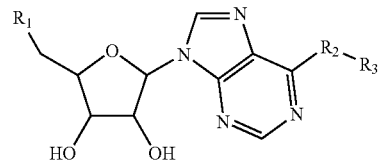

where $R_1$ is OH, monophosphate ($H_2O_3PO-$ or ($O_3PO-)^{2-}$), diphosphate ($H_3(O_3PO)_2-$ or (($O_3PO)_2-)^{3-}$), triphosphate ($H_4(O_3PO)_3-$, (($O_3PO)_3-)^{4-}$), or $OR_a$, where $R_a$ comprises at least one of a straight chain, branched or cyclic alkyl, CO-alkyl, CO-aryl, CO-alkoxyalkyl, arylsulfonyl, aralkylsulfonyl, amino acid residue, fatty acid residue, or a mono, di, or triphosphate derivative;

where $R_2$ is S or O; and where $R_3$ is selected from $C_1$-$C_8$-alkyl, mono- or multisubstituted, alkyl saturated or unsaturated, mono-or multisubstituted or unsubstituted; $C_3$-$C_8$-cycloalkyl or $C_3$-$C_8$-cycloalkyl containing 1 or 2 heteroatoms selected from S, O or N in the ring, mono-or multisubstituted or unsubstituted respectively; phenyl, benzyl, aryl, mono-or multisubstituted or unsubstituted respectively, heteroaryl, mono- or multisubstituted or unsubstituted respectively; and combinations thereof; or a pharmaceutically acceptable salt thereof.

In another aspect of the invention, the inosine analog can be a thioinosine analog that has the following formula (II):

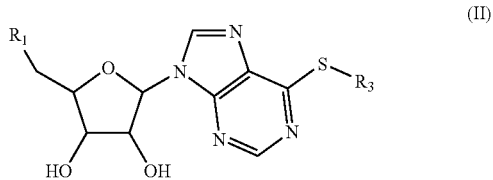

where $R_1$ is OH, monophosphate ($H_2O_3PO-$ or ($O_3PO-)^{2-}$), diphosphate ($H_3(O_3PO)_2-$ or (($O_3PO)_2-)^{3-}$), triphosphate ($H_4(O_3PO)_3-$, (($O_3PO)_3-)^{4-}$), or $OR_a$, where $R_a$ comprises at least one of a straight chain, branched or cyclic alkyl, CO-alkyl, CO-aryl, CO-alkoxyalkyl, arylsulfonyl, aralkylsulfonyl, amino acid residue, fatty acid residue, or a mono, di, or triphosphate derivative; and where $R_3$ can be selected from a $C_1$-$C_6$-alkyl, alkenyl, phenyl, benzyl, aryl, mono-or multisubstituted, respectively.

In a further aspect of the invention, the inosine analog can have the following formula (III):

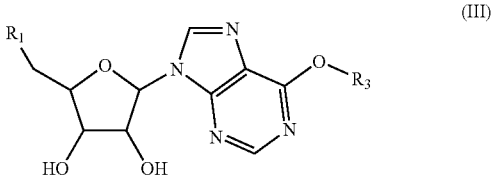

where $R_1$ is OH, monophosphate ($H_2O_3PO-$ or ($O_3PO-)^{2-}$), diphosphate ($H_3(O_3PO)_2-$ or (($O_3PO)_2-)^{3-}$), triphosphate ($H_4(O_3PO)_3$—, $((O_3PO)_3$—$)^{4-}$), or $OR_a$, where $R_a$ comprises at least one of a straight chain, branched or cyclic alkyl, CO-alkyl, CO-aryl, CO-alkoxyalkyl, arylsulfonyl, aralkylsulfonyl, amino acid residue, fatty acid residue, or a mono, di, or triphosphate derivative; and where $R_3$ is selected from a $C_1$-$C_6$-alkyl, alkenyl, phenyl, benzyl, aryl, mono-or multisubstituted, respectively.

In another aspect of the inosine analog has the following formula (IV):

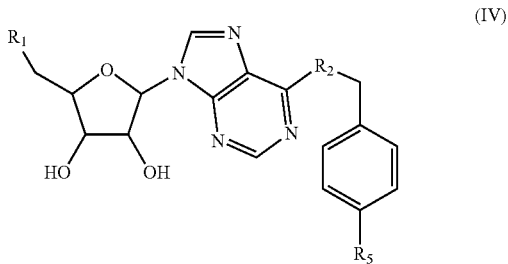

where $R_1$ is OH, monophosphate ($H_2O_3PO$— or ($O_3PO$—$)^{2-}$), diphosphate ($H_3(O_3PO)_2$— or $((O_3PO)_2$—$)^{3-}$), triphosphate ($H_4(O_3PO)_3$—, $((O_3PO)_3$—$)^{4-}$), or $OR_a$, where $R_a$ comprises at least one of a straight chain, branched or cyclic alkyl, CO-alkyl, CO-aryl, CO-alkoxyalkyl, arylsulfonyl, aralkylsulfonyl, amino acid residue, fatty acid residue, or a mono, di, or triphosphate derivative;

where $R_2$ is S or O; and where $R_5$ is a hydrogen, halo, fluoro, alkyl, alkyloxy, nitro, cyano, amino, substituted alkyl, aryl or substituted aryl.

In a still further aspect of the invention, the inosine analog can have the following formula (V),

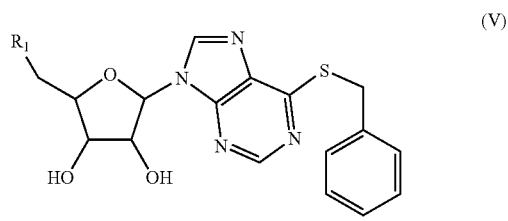

where $R_1$ is OH, monophosphate ($H_2O_3PO$— or ($O_3PO$—$)^{2-}$), diphosphate ($H_3(O_3PO)_2$— or $((O_3PO)_2$—$)^{3-}$), triphosphate ($H_4(O_3PO)_3$—, $((O_3PO)_3$—$)^{4-}$), or $OR_a$, where $R_a$ comprises at least one of a straight chain, branched or cyclic alkyl, CO-alkyl, CO-aryl, CO-alkoxyalkyl, arylsulfonyl, aralkylsulfonyl, amino acid residue, fatty acid residue, or a mono, di, or triphosphate derivative.

The myeloid differentiating agents of the present invention can be used alone or in combination with other differentiating agents or other anti-proliferative agents or chemotherapeutic agents to treat myeloid disorders, such as leukemia, acute myeloid leukemia (AML), myeloproliferative disorders, myelodysplastic disorders, and myeloproliferative/myelodysplastic disorders. The myeloid differentiation agents can also be administered to a subject in conjunction with myeloablative therapy, for example, prior to the subject receiving bone marrow transplantation or stem cell therapy.

The myeloid differentiating agents can also be provided in a pharmaceutical composition either alone or with one or more agents.

BRIEF DESCRIPTION OF THE DRAWINGS

The foregoing and other features of the present invention will become apparent to those skilled in the art to which the present invention relates upon reading the following description with reference to the accompanying drawings, in which:

FIG. 2 illustrates 6BT has growth inhibitory effects on HL-60 cells. A, 6BT inhibits the proliferation of HL-60 cells. Cells were treated with the indicated compounds for 5 d, and the number of cells present at specific times points was assessed by counting at least 200 cells with a hematocytometer. Results shown represent the number of 6BT-treated cells present divided by the number of vehicle-treated cells at specific time points and are an average of three independent experiments. B, 6BT induces alterations of the cell cycle. HL-60 cells were treated with the indicated compounds for 3 d, and the cells were stained with propidium iodide and analyzed by flow cytometry. Results are representative of three independent experiments. C, 6BT leads to the up-regulation of p21 and down-regulation of Bcl-2. HL-60 cells were treated with the indicated compounds for 1, 3, or 5 d, and Western blot analysis was performed on the same membrane with p21, Bcl-2, and β-actin antibodies. D, 6BT inhibits colony formation in soft agar. HL-60 cells were incubated with 6BT or vehicle for 72 h, and the drug was washed off. An equal number of viable cells were added to soft agar, and colony formation was assessed after 10 d. Results are an average of two independent experiments performed in duplicate.

DETAILED DESCRIPTION

Figure 1C:
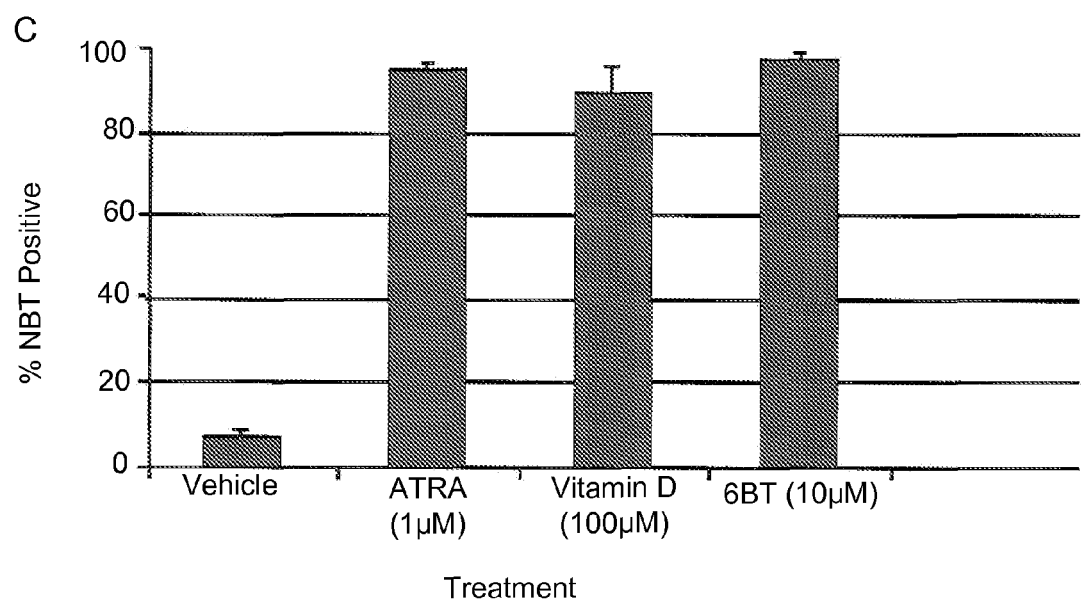
FIG. 1 illustrates that 6BT induces monocyte/macophage differentiation of HL-60 cells. A, 6BT induces morphologic changes consistent with monocyte/macrophage differentiation. After treatment for 4 d with 6BT, cytospin preparations were prepared and the cells were stained with wright-giemsa stain. Magnification, ×40. B, 6BT induces immunophenotypic changes consistent with monocytic differentiation. After treatment for 4 d, HL-60 cells were stained with CD11b-PE and CD14-FITC, and flow cytometric analysis was performed. Results are an average of three independent experiments. C, 6BT induces NBT reduction activity consistent with myelomonocytic differentiation. HL-60 cells were treated with the indicated compounds for 4 d and then the NBT reduction assay was performed. The percentage of NBT-positive cells was calculated by counting at least 200 cells under a light microscope. Results are an average of three independent experiments. D, 6BT induces the monocytic transcription factor CEBP/β and down-regulates the transcription factor c-myc. HL-60 cells were treated for the indicated number of days with vehicle or 10 μmol/L 6BT. The relative expression of CEBP/β and c-myc was determined by real-time PCR.

The present invention relates to compounds or therapeutic agents that can be used to induce differentiation of immature myeloid cells as well as to methods and assays of identifying therapeutic agents or compounds capable of inducing differentiation of immature myeloid cells. Agents in accordance with the invention have a high-potency and low toxicity in mammalian subjects and can be used in the treatment of myeloid disorders, such as leukemia, acute myeloid leukemia (AML), myeloproliferative disorders, myelodysplastic disorders, and myeloproliferative/myelodysplastic disorders myeloproliferative disorders, and auto immune disease, to induce and/or promote differentiation of the myeloid cells. The agents can also be used as a myeloablative agent in conjunction with bone marrow transplantation and stem cell therapies.

The agents in accordance with the present invention can be used alone or in combination with other differentiation inducing agents, anti-proliferative agents, and/or chemotherapeutic agents for the treatment of proliferative and/or other neoplastic disorders.

In an aspect of the present invention, the agents in accordance with the present invention are identified using a novel high-troughput screen that is biased to identify agents that have both a high potency and low toxicity. The screen measures the differentiation of HL-60 leukemic cells using a quantitative nitroblue tetrazolium (NBT) reduction assay. Screening HL-60 cells, human promyelocytic cells, is advantageous as they have been used extensively as a cell line to study myeloid differentiation. Though promyelocytic cells, HL-60 cells are actually derived from a patient with acute myeloblastic leukemia with maturation, FAB-M2. This cell line has been shown to be an excellent model to study myeloid differentiation as it undergoes terminal differentiation to either granulocytic or monocytic pathways with numerous known compounds. The differentiated cells demonstrate all of the expected functional properties such as chemotaxis, bacterial killing, ingestion, and respiratory burst activity.

Nitroblue Tetrazolium (NBT) reduction has been widely demonstrated to provide a very accurate correlation to the extent of myeloid differentiation to both granulocytic and monocytic pathways. This technique has also been widely exploited in HL-60 cells to analyze myelomonocytic differentiation. In fact, it has been routinely demonstrated for over 20 years that the NBT test provides an extremely close correlation with the morphology of the differentiated cells.

The NBT screen works due to changes in the oxidoreductases during differentiation that lead to increases in rates of NBT reduction. NBT is reduced due to the production of superoxide that is catalyzed by an NADPH oxidase. This enzyme is inactive in resting cells, therefore, it is necessary to treat the cells with PMA to generate an oxidative burst. NBT is reduced by superoxide from a soluble yellow compound to isoluble blue formazan granules whose formation can be monitored spectrophotometrically at 560 nm as the unreduced dye has minimal absorbance at this wavelength. A quantitative NBT reduction assay is ideal for this type of screen as it is simple, sensitive, quantitative, requires minimal cells, has been proven to have low well to well variability, and the amount of reduced NBT is proportional to the number of cells reducing the dye as well as the amount reduced by each cell.

By way of example, duplicate plates of HL-60 cells can be cultured at a density of $5 \times 10^4$ cells/ml with 10 µM of each compound in 96 well plates for 5 days. To determine the relative capability for a compound to induce differentiation compared to known potent inducers, each plate destined for the NBT reduction assay can include wells with 0.1% DMSO (vehicle control) and 1 µM ATRA. This approach eliminates any slight day to day variation in NBT reduction values and allows the discovery of compounds with similar or greater efficacy to ATRA. Differentiation is determined in the 96 well plates by incubating the cells with 1 mg/ml of NBT and 200 ng/ml of PMA as the stimulant for the respiratory burst for 35 minutes at 37° C. The reaction can then be stopped with HCL and the formazan will be solubilized with DMSO. Finally, the reaction mixture will be read spectrophotometricaly at 560 nm in a plate reader.

In accordance with an aspect of the invention, agents identified using the screen of the present invention that exhibit high potency and low toxicity and that can be used to induce differentiation of immature myeloid cells include inosine analogs having the following general formula (I):

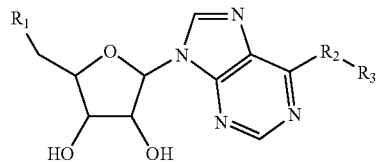

where $R_1$ is OH, monophosphate ($H_2O_3PO-$ or ($O_3PO-)^{2-}$), diphosphate ($H_3(O_3PO)_2-$ or (($O_3PO)_2-)^{3-}$), triphosphate ($H_4(O_3PO)_3-$, (($O_3PO)_3-)^{4-}$), or $OR_a$, where $R_a$ comprises at least one of a straight chain, branched or cyclic alkyl, CO-alkyl, CO-aryl, CO-alkoxyalkyl, arylsulfonyl, aralkylsulfonyl, amino acid residue, fatty acid residue, or a mono, di, or triphosphate derivative;

where $R_2$ is S or O; and where $R_3$ is selected from $C_1$-$C_8$-alkyl, mono- or multisubstituted, alkyl saturated or unsaturated, mono-or multisubstituted or unsubstituted; $C_3$-$C_8$-cycloalkyl or $C_3$-$C_8$-cycloalkyl containing 1 or 2 heteroatoms selected from S, O or N in the ring, mono-or multisubstituted or unsubstituted respectively; phenyl, benzyl, aryl, mono-or multisubstituted or unsubstituted respectively, heteroaryl, mono-or multisubstituted or unsubsubstituted respectively; and combinations thereof; or a pharmaceutically acceptable salt thereof.

The phrase "having the formula" or "having the structure" is not intended to be limiting and is used in the same way that the term "comprising" is commonly used.

The term "alkyl" refers to a branched or unbranched saturated hydrocarbon group, such as methyl, ethyl, n-propyl, isopropyl, n-butyl, isobutyl, t-butyl, octyl, decyl, and the like, as well "Substituted alkyl" refers to alkyl substituted with one or more substituent groups, and the terms "heteroatom-containing alkyl" and "heteroalkyl" refer to alkyl in which at least one carbon atom is replaced with a heteroatom, as described in further detail infra. If not otherwise indicated, the terms "alkyl" and "lower alkyl" include linear, branched, cyclic, unsubstituted, substituted, and/or heteroatom-containing alkyl or lower alkyl, respectively.

The term "aryl" refers to an aromatic substituent containing a single aromatic ring or multiple aromatic rings that are fused together, directly linked, or indirectly linked (such that the different aromatic rings are bound to a common group such as a methylene or ethylene moiety). Aryl groups can contain 5 to 20 carbon atoms, and particularly preferred aryl groups can contain 5 to 14 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl, in which at least one carbon atom is replaced with a heteroatom, as will be described in further detail infra. If not otherwise indicated, the term "aryl" includes unsubstituted, substituted, and/or heteroatom-containing aromatic substituents.

The term "cyclic" refers to alicyclic or aromatic substituents that may or may not be substituted and/or heteroatom containing, and that may be monocyclic, bicyclic, or polycyclic.

The terms "halo" and "halogen" are used in the conventional sense to refer to a chloro, bromo, fluoro or iodo substituent.

The term "heteroatom-containing" as in a "heteroatom-containing alkyl group" (also termed a "heteroalkyl" group) or a "heteroatom-containing aryl group" (also termed a "heteroaryl" group) refers to a molecule, linkage or substituent in which one or more carbon atoms are replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and heteroaromatic" respectively refer to "aryl" and "aromatic" substituents that are heteroatom-containing, and the like. Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups are pyrrolidino, morpholino, piperazino, piperidino, etc.

By "substituted" as in "substituted alkyl," "substituted aryl," and the like, as alluded to in some of the aforementioned definitions, is meant that in the alkyl, aryl, or other moiety, at least one hydrogen atom bound to a carbon (or other) atom is replaced with one or more non-hydrogen substituents. Examples of such substituents include, without limitation: functional groups such as halo, hydroxyl, silyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_4$ alkyl)-substituted carbamoyl (—(CO)—N($C_1$-$C_{24}$ alkyl)$_2$), mono-substituted arylcarbamoyl (—(CO)—NH-aryl), thiocarbamoyl (—(SC)—NH$_2$), carbamido (—NH—(CO)—NH$_2$), cyano(—CN), isocyano (—N$^+$C$^-$), cyanato (—O—CN), isocyanato (—ON$^+$C$^-$), isothiocyanato (—S—CN), azido (—N=N$^+$=N$^-$), formyl (—(CO)—H), thioformyl (—(CS)—H), amino (—NH$_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_6$-$C_{20}$ arylamido (—NH—(CO)-aryl), imino (—CR=NH where R=hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), phosphono (—P(O)(OH)$_2$), phosphonato (—P(O)(O$^-$)$_2$), phosphinato (—P(O)(O$^-$)), phospho (—PO$_2$), and phosphino (—PH$_2$); and the hydrocarbyl moieties $C_1$-$C_{24}$ alkyl, $C_2$-$C_{24}$ alkenyl, $C_2$-$C_{24}$ alkynyl, $C_5$-$C_{20}$ aryl, $C_6$-$C_{24}$ alkaryl, and $C_6$-$C_{24}$ aralkyl.

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

When the term "substituted" appears prior to a list of possible substituted groups, it is intended that the term apply to every member of that group. For example, the phrase "substituted alkyl, alkenyl, and aryl" is to be interpreted as "substituted alkyl, substituted alkenyl, and substituted aryl." Analogously, when the term "heteroatom-containing" appears prior to a list of possible heteroatom-containing groups, it is intended that the term apply to every member of that group. For example, the phrase "heteroatom-containing alkyl, alkenyl, and aryl" is to be interpreted as "heteroatom-containing alkyl, substituted alkenyl, and substituted aryl."

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

Some of the agents disclosed herein may contain one or more asymmetric centers and may thus give rise to enantiomers, diastereomers, and other stereoisomeric forms. The present invention is also meant to encompass racemic mixtures, resolved forms and mixtures thereof, as well as the individual enantiomers that may be separated according to methods that are well know to those of ordinary skill in the art. When the agents described herein contain olefinic double bonds or other centers of geometric asymmetry, and unless specified otherwise, it is intended to include both E and Z geometric isomers.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "asymmetric center" or "chiral center" refers to a carbon atom to which four different groups are attached.

The term "enantiomer" or "enantiomeric" refers to a molecule that is nonsuperimposeable on its mirror image and hence optically active wherein the enantiomer rotates the plane of polarized light in one direction and its mirror image rotates the plane of polarized light in the opposite direction.

The term "racemic" refers to a mixture of equal parts of enantiomers and which is optically inactive.

The term "resolution" refers to the separation or concentration or depletion of one of the two enantiomeric forms of a molecule. The phrase "enantiomeric excess" refers to a mixture wherein one enantiomer is present is a greater concentration than its mirror image molecule.

In another aspect of the present invention, the inosine analog can be a thioinosine that can have the following formula (II):

(II)

where $R_1$ is OH, monophosphate ($H_2O_3PO-$ or ($O_3PO-$)$^{2-}$), diphosphate ($H_3(O_3PO)_2-$ or (($O_3PO)_2-$)$^{3-}$), triphosphate ($H_4(O_3PO)_3-$, (($O_3PO)_3-$)$^{4-}$), or $OR_a$, where $R_a$ comprises at least one of a straight chain, branched or cyclic alkyl, CO-alkyl, CO-aryl, CO-alkoxyalkyl, arylsulfonyl, aralkylsulfonyl, amino acid residue, fatty acid residue, or a mono, di, or triphosphate derivative; and where $R_3$ is selected from a mono- or multisubstituted, alkyl, saturated or unsaturated, mono-or multisubstituted or unsubstituted $C_3$-$C_8$-cycloalkyl or $C_3$-$C_8$-cycloalkyl containing 1 or 2 heteroatoms selected from S, O or N in the ring, mono-or multisubstituted or unsubstituted respectively; phenyl or benzyl, mono-or multisubstituted or unsubstituted respectively phenyl, benzyl, aryl, heteroaryl, mono-or multisubstituted or unsubsubstituted respectively.

In a still further aspect of the invention, $R_3$ can be selected from a $C_1$-$C_6$-alkyl (e.g., methyl), alkenyl, phenyl, benzyl, aryl, mono-or multisubstituted, respectively. Examples of thioinsone analogs in accordance with formula (II) include 6-benzylthioinosine, 6-ethylthioinosine, 6-propenylthioinosine, and 6-methylthioinosine.

In another aspect of the present invention, the inosine analog can have the following formula (III):

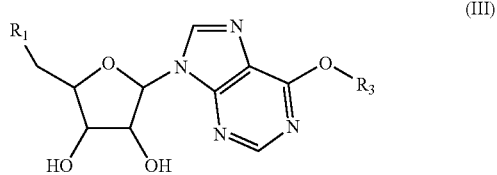

(III)

where $R_1$ is OH, monophosphate ($H_2O_3PO-$ or ($O_3PO-$)$^{2-}$), diphosphate ($H_3(O_3PO)_2-$ or (($O_3PO)_2-$)$^{3-}$), triphosphate ($H_4(O_3PO)_3-$, (($O_3PO)_3-$)$^{4-}$), or $OR_a$, where $R_a$ comprises at least one of a straight chain, branched or cyclic alkyl, CO-alkyl, CO-aryl, CO-alkoxyalkyl, arylsulfonyl, aralkylsulfonyl, amino acid residue, fatty acid residue, or a mono, di, or triphosphate derivative; and where $R_3$ is selected from a mono- or multisubstituted, alkyl, saturated or unsaturated, mono-or multisubstituted or unsubstituted $C_3$-$C_8$-cycloalkyl or $C_3$-$C_8$-cycloalkyl containing 1 or 2 heteroatoms selected from S, O or N in the ring, mono-or multisubstituted or unsubstituted respectively; phenyl or benzyl, mono-or multisubstituted or unsubstituted respectively phenyl, benzyl, aryl, heteroaryl, mono-or multisubstituted or unsubsubstituted respectively.

In a still further aspect of the invention, $R_3$ can be selected from a $C_1$-$C_6$-alkyl (e.g., methyl), alkenyl, phenyl, benzyl, aryl, mono-or multisubstituted, respectively.

In another aspect of the present invention, the inosine analog can have the following formula (IV):

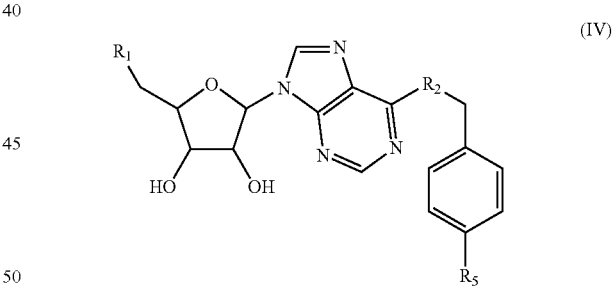

(IV)

where $R_1$ is OH, monophosphate ($H_2O_3PO-$ or ($O_3PO-$)$^{2-}$), diphosphate ($H_3(O_3PO)_2-$ or (($O_3PO)_2-$)$^{3-}$), triphosphate ($H_4(O_3PO)_3-$, (($O_3PO)_3-$)$^{4-}$), or $OR_a$, where $R_a$ comprises at least one of a straight chain, branched or cyclic alkyl, CO-alkyl, CO-aryl, CO-alkoxyalkyl, arylsulfonyl, aralkylsulfonyl, amino acid residue, fatty acid residue, or a mono, di, or triphosphate derivative;

where $R_2$ is S or O; and where $R_5$ is a hydrogen, halo (e.g., Cl, Br, etc.), fluoro, alkyl, alkyloxy, nitro, cyano, amino, substituted alkyl, aryl or substituted aryl.

In yet another aspect of the invention, the inosine analog can be substituted or unsubstituted 6-benzylthioinosine having the following formula (V),

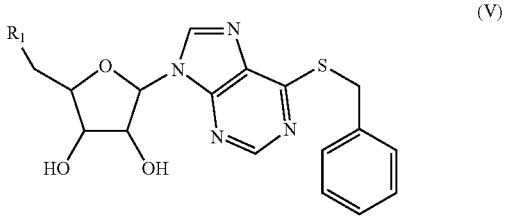

(V)

where $R_1$ is OH, monophosphate ($H_2O_3PO-$ or ($O_3PO-)^{2-}$), diphosphate ($H_3(O_3PO)_2-$ or $((O_3PO)_2-)^{3-}$), triphosphate ($H_4(O_3PO)_3-$, $((O_3PO)_3-)^{4-}$), or $OR_a$, where $R_a$ comprises at least one of a straight chain, branched or cyclic alkyl, CO-alkyl, CO-aryl, CO-alkoxyalkyl, arylsulfonyl, aralkylsulfonyl, amino acid residue, fatty acid residue, or a mono, di, or triphosphate derivative.

The inosine analog myeloid differentiation agents in accordance with the present can be administered in a therapeutically effective amount to a patient or subject with a disorder characterized by arrest of differentiation of immature myeloid cells. These disorders can include, for example, myeloproliferative diserorders, such as leukemia, and immunity related diseases.

The term "therapeutic" refers to reduction in severity and/or frequency of symptoms, elimination of symptoms and/or underlying cause, prevention of the occurrence of symptoms and/or their underlying cause, and improvement or remediation of disease. For example, treatment of a patient by administration of myeloid differentiation agent of the present invention encompasses chemoprevention in a patient susceptible to developing myeloid leukemia (e.g., at a higher risk, as a result of genetic predisposition, environmental factors, or the like) and/or in cancer survivors at risk of cancer recurrence, as well as treatment of a myeloid leukemia patient by inhibiting or causing regression of a disorder or disease.

"Effective amounts", in terms of each of the foregoing methods, are amounts of the myeloid differentiation agent effective to induce or promote differentiation of the immature myeloid cells in the subject being treated without being cytotoxic to the subject.

The immature myeloid differentiation inducing agents of the present invention can be provided in the form of pharmaceutical compositions. The pharmaceutical compositions can be administered to any mammal that can experience the beneficial effects of the myeloid differentiation inducing agents of the present invention. Foremost among such animals are humans, although the present invention is not intended to be so limited.

The pharmaceutical compositions of the present invention can be administered by any means that achieve their intended purpose. For example, administration can be by parenteral, subcutaneous, intravenous, intraarticular, intrathecal, intramuscular, intraperitoneal, or intradermal injections, or by transdermal, buccal, oromucosal, ocular routes or via inhalation. Alternatively or concurrently, administration can be by the oral route. Particularly preferred is oral administration. The dosage administered will be dependent upon the age, health, and weight of the patient, kind of concurrent treatment, if any, frequency of treatment, and the nature of the effect desired.

In addition to the pharmacologically active compounds, the pharmaceutical preparations of the myeloid differentiation inducing agents can contain suitable pharmaceutically acceptable carriers comprising excipients and auxiliaries that facilitate processing of the active agents into preparations that can be used pharmaceutically. The pharmaceutical preparations of the present invention are manufactured in a manner that is, itself, known, for example, by means of conventional mixing, granulating, dragee-making, dissolving, or lyophilizing processes. Thus, pharmaceutical preparations for oral use can be obtained by combining the active agents with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example, lactose or sucrose, mannitol or sorbitol, cellulose preparations and/or calcium phosphates, for example, tricalcium phosphate or calcium hydrogen phosphate, as well as binders, such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents can be added, such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings, that, if desired, are resistant to gastric juices. For this purpose, concentrated saccharide solutions can be used, which may optionally contain gum arabic, talc, polyvinyl pyrrolidone, polyethylene glycol, and/or titanium dioxide, lacquer solutions and suitable organic solvents or solvent mixtures. In order to produce coatings resistant to gastric juices, solutions of suitable cellulose preparations, such as acetylcellulose phthalate or hydroxypropylmethylcellulose phthalate, are used. Slow-release and prolonged-release formulations may be used with particular excipients such as methacrylic acid-ethylacrylate copolymers, methacrylic acid-ethyl acrylate copolymers, methacrylic acid-methyl methacrylate copolymers and methacrylic acid-methyl methylacrylate copolymers. Dye stuffs or pigments can be added to the tablets or dragee coatings, for example, for identification or in order to characterize combinations of active compound doses.

Other pharmaceutical preparations that can be used orally include push-fit capsules made of gelatin, as well as soft, sealed capsules made of gelatin and a plasticizer such as glycerol or sorbitol. The push-fit capsules can contain the active compounds in the form of granules that may be mixed with fillers such as lactose, binders such as starches, and/or lubricants such as talc or magnesium stearate and, optionally, stabilizers. In soft capsules, the active compounds are preferably dissolved or suspended in suitable liquids such as fatty oils or liquid paraffin. In addition, stabilizers may be added.

Formulations for parenteral administration include aqueous solutions of the active compounds in water-soluble form, for example, water-soluble salts and alkaline solutions. Especially preferred salts are maleate, fumarate, succinate, S,S tartrate, or R,R tartrate. In addition, suspensions of the active compounds as appropriate oily injection suspensions can be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400). Aqueous injection suspensions can contain substances that increase the viscosity of the suspension, for example sodium carboxymethyl cellulose, sorbitol, and/or dextran. Optionally, the suspension may also contain stabilizers.

In a further aspect of the invention, the myeloid differentiation inducing agents can be used in combination and adjunctive therapies for treating proliferative disorders.

The phrase "combination therapy" embraces the administration of the myeloid differentiation inducing agents and a therapeutic agent as part of a specific treatment regimen intended to provide a beneficial effect from the co-action of these therapeutic agents. Administration of these therapeutic agents in combination typically is carried out over a defined time period (usually minutes, hours, days or weeks depending upon the combination selected). "Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical. "Combination therapy" also can embrace the administration of the therapeutic agents as described above in further combination with other biologically active ingredients (such as, but not limited to, a second and different therapeutic agent) and non-drug therapies (such as, but not limited to, surgery or radiation treatment). Where the combination therapy further comprises radiation treatment, the radiation treatment may be conducted at any suitable time so long as a beneficial effect from the co-action of the combination of the therapeutic agents and radiation treatment is achieved. For example, in appropriate cases, the beneficial effect is still achieved when the radiation treatment is temporally removed from the administration of the therapeutic agents, perhaps by days or even weeks.

The phrase "adjunctive therapy" encompasses treatment of a subject with agents that reduce or avoid side effects associated with the combination therapy of the present invention, including, but not limited to, those agents, for example, that reduce the toxic effect of anticancer drugs, e.g., bone resorption inhibitors, cardioprotective agents; prevent or reduce the incidence of nausea and vomiting associated with chemotherapy, radiotherapy or operation; or reduce the incidence of infection associated with the administration of myelosuppressive anticancer drugs.

The mammalian disease treated by the combination therapy can include proliferative diseases, such as neoplastic disorders (e.g., leukemia) and autoimmune dysfunctions as well as viral and microbial infections. Besides being useful for human treatment, the combination therapy is also useful for veterinary treatment of companion animals, exotic and farm animals, including rodents, horses, dogs, and cats.

In another aspect of the invention, the therapeutic agents administered in combination therapy with the myeloid differentiation inducing agents can comprise at least one anti-proliferative agent selected from the group consisting of a chemotherapeutic agent, an antimetabolite, an antitumorgenic agent, an antimitotic agent, an antiviral agent, an antineoplastic agent, an immunotherapeutic agent, and a radiotherapeutic agent.

The phrase "anti-proliferative agent" can include agents that exert antineoplastic, chmotherapeutic, antiviral, antimitotic, antitumorgenic, and/or immunotherapeutic effects, e.g., prevent the development, maturation, or spread of neoplastic cells, directly on the tumor cell, e.g., by cytostatic or cytocidal effects, and not indirectly through mechanisms such as biological response modification. There are large numbers of anti-proliferative agent agents available in commercial use, in clinical evaluation and in pre-clinical development, which could be included in the present invention by combination drug chemotherapy. For convenience of discussion, anti-proliferative agents are classified into the following classes, subtypes and species: ACE inhibitors, alkylating agents, angiogenesis inhibitors, angiostatin, anthracyclines/DNA intercalators, anti-cancer antibiotics or antibiotic-type agents, antimetabolites, antimetastatic compounds, asparaginases, bisphosphonates, cGMP phosphodiesterase inhibitors, calcium carbonate, cyclooxygenase-2 inhibitors, DHA derivatives, DNA topoisomerase, endostatin, epipodophylotoxins, genistein, hormonal anticancer agents, hydrophilic bile acids (URSO), immunomodulators or immunological agents, integrin antagonists, interferon antagonists or agents, MMP inhibitors, miscellaneous antineoplastic agents, monoclonal antibodies, nitrosoureas, NSAIDs, ornithine decarboxylase inhibitors, pBATTs, radio/chemo sensitizers/protectors, retinoids, selective inhibitors of proliferation and migration of endotheliai cells, selenium, stromelysin inhibitors, taxanes, vaccines, and vinca alkaloids.

The major categories that some anti-proliferative agents fall into include antimetabolite agents, alkylating agents, antibiotic-type agents, hormonal anticancer agents, immunological agents, interferon-type agents, and a category of miscellaneous antineoplastic agents. Some anti-proliferative agents operate through multiple or unknown mechanisms and can thus be classified into more than one category.

A first family of anti-proliferative agents, which may be used in combination therapy with the myeloid differentiation inducing agents consists of antimetabolite-type anti-proliferative agents. Antimetabolites are typically reversible or irreversible enzyme inhibitors, or compounds that otherwise interfere with the replication, translation or transcription of nucleic acids. Such compounds can include, for example, nucleoside anlogs. Examples of antimetabolite anti-proliferative agents that may be used in the present invention include, but are not limited to acanthifolic acid, aminothiadiazole, anastrozole, bicalutamide, brequinar sodium, capecitabine, carmofur, Ciba-Geigy CGP-30694, cladribine, cyclopentyl cytosine, cytarabine (ARA-C), cytarabine phosphate stearate, cytarabine conjugates, cytarabine ocfosfate, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, finasteride, floxuridine, fludarabine, fludarabine phosphate, N-(2'-furanidyl)-5-fluorouracil, Daiichi Seiyaku FO-152, fluorouracil (5-FU), 5-FU-fibrinogen, isopropyl pyrrolizine, Lilly LY-188011, Lilly LY-264618, methobenzaprim, methotrexate, Wellcome MZPES, nafarelin, norspermidine, nolvadex, NCI NSC-127716, NCI NSC-264880, NCI NSC-39661, NCI NSC-612567, Warner-Lambert PALA, pentostatin, piritrexim, plicamycin, Asahi Chemical PL-AC, stearate; Takeda TAC-788, thioguanine, tiazofurin, Erbamont TIF, trimetrexate, tyrosine kinase inhibitors, tyrosine protein kinase inhibitors, Taiho UFT, toremifene, uricytin, and vidarbine all of which are disclosed in U.S. Pat. No. 6,916,800, which is herein incorporated by reference in its entirety.

A second family of anti-proliferative agents, which may be used in combination therapy with the myeloid differentiation inducing agents of the present invention consists of alkylating-type anti-proliferative agents. The alkylating agents are believed to act by alkylating and cross-linking guanine and possibly other bases in DNA, arresting cell division. Typical alkylating agents include nitrogen mustards, ethyleneimine compounds, alkyl sulfates, cisplatin, and various nitrosoureas. A disadvantage with these compounds is that they not only attack malignant cells, but also other cells which are naturally dividing, such as those of bone marrow, skin, gastro-intestinal mucosa, and fetal tissue. Examples of alkylating-type anti-proliferative agents that may be used in the present invention include, but are not limited to, Shionogi 254-S, aldo-phosphamide analogues, altretamine, anaxirone, Boehringer Mannheim BBR-2207, bestrabucil, budotitane, Wakunaga CA-102, carboplatin, carmustine (BiCNU), Chinoin-139, Chinoin-153, chlorambucil, cisplatin, cyclophosphamide, American Cyanamid CL-286558, Sanofi CY-233, cyplatate, dacarbazine, Degussa D-19-384, Sumimoto DACHP(Myr)2, diphenylspiromustine, diplatinum cytostatic, Erba distamycin derivatives, Chugai DWA-2114R, ITI E09, elmustine, Erbamont FCE-24517, estramustine phosphate sodium, etoposide phosphate, fotemustine, Unimed G-6-M, Chinoin GYKI-17230, hepsul-fam, ifosfamide, iproplatin, lomustine, mafosfamide, mitolactol, mycophenolate, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, thiotepa, Yakult Honsha SN-22, spiromus-tine, Tanabe Seiyaku TA-077, tauromustine, temozolomide, teroxirone, tetraplatin and trimelamol.

A third family of anti-proliferative agents that may be used in combination therapy with the myeloid differentiation inducing agents of the present invention consists of antibiotic-type anti-proliferative agents. Examples of antibiotic-type anti-proliferative agents that may be used in the present invention include, but are not limited to Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-A1b, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindamycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 and zorubicin.

A fourth family of anti-proliferative agents that may be used in combination therapy with the myeloid differentiation inducing agents of the present invention consists of hormonal agents. Examples of hormonal-type anti-proliferative agents that may be used in the present invention include, but are not limited to Abarelix; Abbott A-84861; Abiraterone acetate; Aminoglutethimide; anastrozole; Asta Medica AN-207; Antide; Chugai AG-041R; Avorelin; aseranox; Sensus B2036-PEG; Bicalutamide; buserelin; BTG CB-7598; BTG CB-7630; Casodex; cetrolix; clastroban; clodronate disodium; Cosudex; Rotta Research CR-1505; cytadren; crinone; deslorelin; droloxifene; dutasteride; Elimina; Laval University EM-800; Laval University EM-652; epitiostanol; epristeride; Mediolanum EP-23904; EntreMed 2-ME; exemestane; fadrozole; finasteride; flutamide; formestane; Pharmacia & Upjohn FCE-24304; ganirelix; goserelin; Shire gonadorelin agonist; Glaxo Wellcome GW-5638; Hoechst Marion Roussel Hoe-766; NCI hCG; idoxifene; isocordoin; Zeneca ICI-182780; Zeneca ICI-118630; Tulane University J015X; Schering Ag J96; ketanserin; lanreotide; Milkhaus LDI-200; letrozol; leuprolide; leuprorelin; liarozole; lisuride hydrogen maleate; loxiglumide; mepitiostane; Leuprorelin; Ligand Pharmaceuticals LG-1127; LG-1447; LG-2293; LG-2527; LG-2716; Bone Care International LR-103; Lilly LY-326315; Lilly LY-353381-HCl; Lilly LY-326391; Lilly LY-353381; Lilly LY-357489; miproxifene phosphate; Orion Pharma MPV-2213ad; Tulane University MZ-4-71; nafarelin; nilutamide; Snow Brand NKS01; octreotide; Azko Nobel ORG-31710; Azko Nobel ORG-31806; orimeten; orimetene; orimetine; ormeloxifene; osaterone; Smithkline Beecham SKB-105657; Tokyo University OSW-1; Peptech PTL-03001; Pharmacia & Upjohn PNU-156765; quinagolide; ramorelix; Raloxifene; statin; sandostatin LAR; Shionogi S-10364; Novartis SMT-487; somavert; somatostatin; tamoxifen; tamoxifen methiodide; teverelix; toremifene; triptorelin; TT-232; vapreotide; vorozole; Yamanouchi YM-116; Yamanouchi YM-511; Yamanouchi YM-55208; Yamanouchi YM-53789; Schering AG ZK-1911703; Schering AG ZK-230211; and Zeneca ZD-182780.

A fifth family of anti-proliferative agents that may be used in combination therapy with the myeloid differentiation inducing agents of the present invention consists of a miscellaneous family of antineoplastic agents including, but not limited to alpha-carotene, alpha-difluoromethyl-arginine, acitretin, Biotec AD-5, Kyorin AHC-52, alstonine, amonafide, amphethinile, amsacrine, Angiostat, ankinomycin, antineoplaston A10, antineoplaston A2, antineoplaston A3, antineoplaston A5, antineoplaston AS2-1, Henkel APD, aphidicolin glycinate, asparaginase, Avarol, baccharin, batracylin, benfluron, benzotript, Ipsen-Beaufour BIM-23015, bisantrene, Bristo-Myers BMY-40481, Vestar boron-10, bromofosfamide, Wellcome BW-502, Wellcome BW-773, calcium carbonate, Calcet, Calci-Chew, Calci-Mix, Roxane calcium carbonate tablets, caracemide, carmethizole hydrochloride, Ajinomoto CDAF, chlorsulfaquinoxalone, Chemes CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Cell Pathways CP-461, Yakult Honsha CPT-11, crisnatol, curaderm, cytochalasin B, cytarabine, cytocytin, Merz D-609, DABIS maleate, dacarbazine, datelliptinium, DFMO, didemnin-B, dihaematoporphyrin ether, dihydrolenperone, dinaline, distamycin, Toyo Pharmar DM-341, Toyo Pharmar DM-75, Daiichi Seiyaku DN-9693, docetaxel, Encore Pharmaceuticals E7869, elliprabin, elliptinium acetate, Tsumura EPMTC, ergotamine, etoposide, etretinate, Eulexin®, Cell Pathways Exisulind® (sulindac sulphone or CP-246), fenretinide, Merck Research Labs Finasteride, Florical, Fujisawa FR-57704, gallium nitrate, gemcitabine, genkwadaphnin, Gerimed, Chugai GLA-43, Glaxo GR-63178, grifolan NMF-5N, hexadecylphosphocholine, Green Cross HO-221, homoharringtonine, hydroxyurea, BTG ICRF-187, ilmofosine, irinotecan, isoglutamine, isotretinoin, Otsuka JI-36, Ramot K-477, ketoconazole, Otsuak K-76COONa, Kureha Chemical K-AM, MECT Corp KI-8110, American Cyanamid L-623, leucovorin, levamisole, leukoregulin, lonidamine, Lundbeck LU-23-112, Lilly LY-186641, Materna, NCI (US) MAP, marycin, Merrel Dow MDL-27048, Medco MEDR-340, megestrol, merbarone, merocyanine derivatives, methylanilinoacridine, Molecular Genetics MGI-136, minactivin, mitonafide, mitoquidone, Monocal, mopidamol, motretinide, Zenyaku Kogyo MST-16, Mylanta, N-(retinoyl)amino acids, Nilandron; Nisshin Flour Milling N-021, N-acylated-dehydroalanines, nafazatrom, Taisho NCU-190, Nephro-Calci tablets, nocodazole derivative, Normosang, NCI NSC-145813, NCI NSC-361456, NCI NSC-604782, NCI NSC-95580, octreotide, Ono ONO-112, oquizanocine, Akzo Org-10172, paclitaxel, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, retinoids, Encore Pharmaceuticals R-flurbiprofen, Sandostatin; Sapporo Breweries RBS, restrictin-P, retelliptine, retinoic acid, Rhone-Poulenc RP-49532, Rhone-Poulenc RP-56976, Scherring-Plough SC-57050, Scherring-Plough SC-57068, seienium(selenite and selenomethionine), SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, Sugen SU-101, Sugen SU-5416, Sugen SU-6668, sulindac, sulindac sulfone; superoxide dismutase, Toyama T-506, Toyama T-680, taxol, Teijin TEI-0303, teniposide, thaliblastine, Eastman Kodak TJB-29, tocotrienol, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides, Yamanouchi YM-534, Zileuton, ursodeoxycholic acid, and Zanosar.

The myeloid differentiation inducing agents in accordance with the present invention can allow the combination therapeutic agents and therapies of the present invention to be administered at a low dose, that is, at a dose lower than has been conventionally used in clinical situations.

A benefit of lowering the dose of the combination therapeutic agents and therapies of the present invention administered to a mammal includes a decrease in the incidence of adverse effects associated with higher dosages. For example, by the lowering the dosage of a chemotherapeutic agent such as methotrexate, a reduction in the frequency and the severity of nausea and vomiting will result when compared to that observed at higher dosages. Similar benefits are contemplated for the compounds, compositions, agents and therapies in combination with the inhibitors of the present invention.

By lowering the incidence of adverse effects, an improvement in the quality of life of a patient undergoing treatment for cancer is contemplated. Further benefits of lowering the incidence of adverse effects include an improvement in patient compliance, a reduction in the number of hospitalizations needed for the treatment of adverse effects, and a reduction in the administration of analgesic agents needed to treat pain associated with the adverse effects.

Alternatively, the methods and combination of the present invention can also maximize the therapeutic effect at higher doses.

When administered as a combination, the therapeutic agents can be formulated as separate compositions, which are given at the same time or different times, or the therapeutic agents can be given as a single composition.

This invention is further illustrated by the following examples, which should not be construed as limiting. The contents of all references, patent applications, patents, and published patent applications cited throughout this application are hereby incorporated by reference in their entirety.

EXAMPLES

To discover clinically useful differentiation-inducing agents, we screened ~6,000 compounds taken from several small compound collections. The phenotypic screen assessed differentiation by measuring the functional maturation of HL-60 leukemic cells by the NBT reduction assay, a test that is highly specific to and has been used extensively as a measure of functional myelomonocytic differentiation. The NBT reduction test measures the ability of cells to generate a respiratory burst, a function that is only present in differentiated cells.

6BT Induced Myeloid Differentiation.

One compound in particular, 6BT, exhibited clinical potential. 6BT induced differentiation of HL-60 myeloid leukemia cells as shown by morphology, immunophenotyping, and NBT reduction (FIG. 1). Clear morpho-logic monocyte/macrophage differentiation was shown by such features as condensed nuclei, abundant cytoplasm, and vacuoles (FIG. 1A). In addition, 6BT induced cells to adhere to the tissue culture plate Immunophenotyping with CD11b, which is upregulated during myelomonocytic differentiation, and CD 14, which is up-regulated primarily during monocytic differentiation, further confirmed the differentiation pathway. All-trans retinoic acid (ATRA), which induced granulocytic differentiation, induces primarily CD11b expression, whereas 6BT and vitamin D3, which induce monocytic differentiation, lead to up-regulation of both CD11b and CD14 expression (FIG. 1B). 6BT exhibits similar differentiation-inducing activity to the highly active differentiation agents ATRA and vitamin D3 as measured by NBT reduction with 6BT differentiating 97%±1.9%, ATRA differentiating 95%±1.7%, and Vitamin D3 differentiating 91%±4.6% of HL-60 cells (FIG. 1C).

Figure 1D:
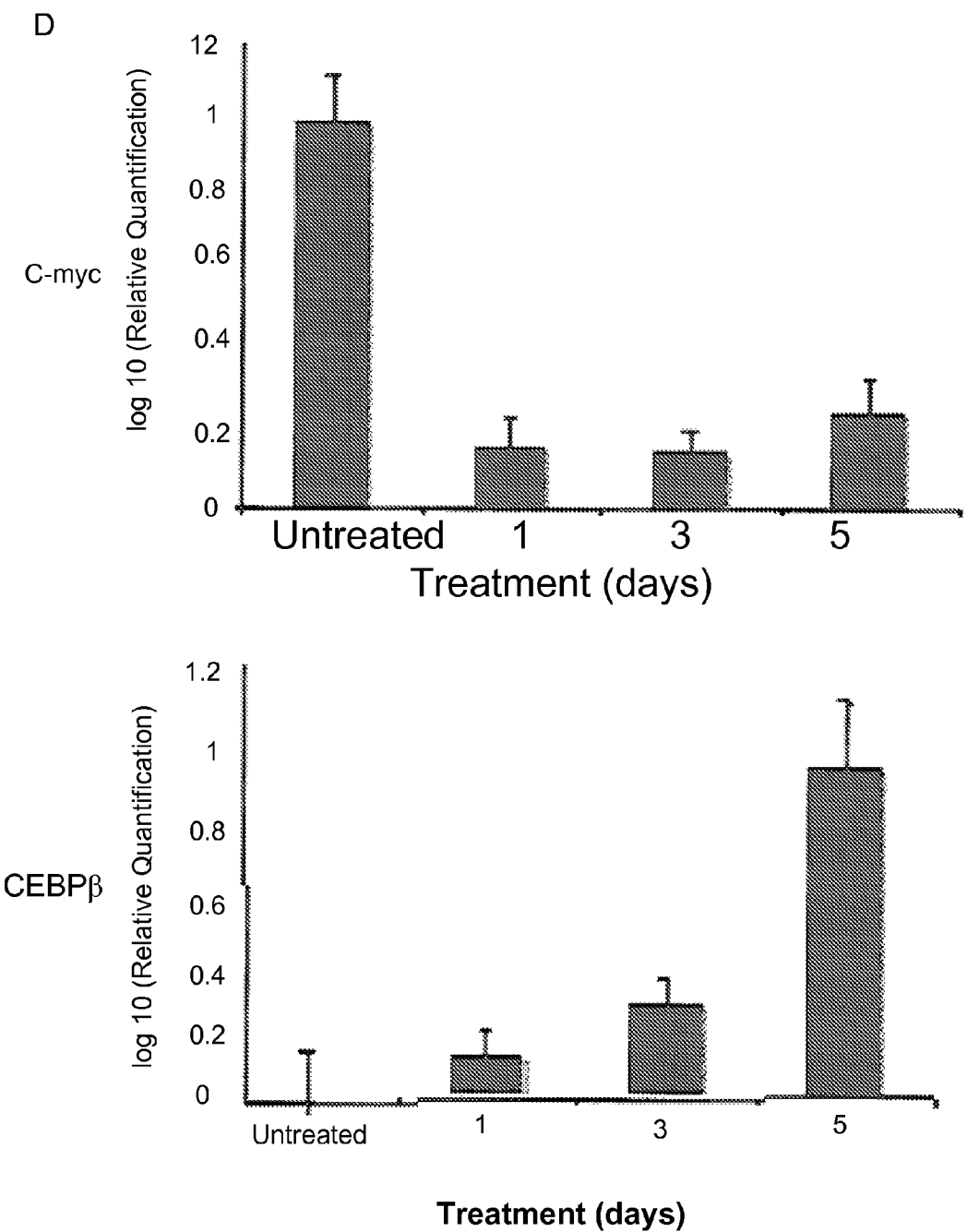

To further examine the ability of 6BT to induce myeloid differentiation, its effects on the transcription factors CEBP/β and c-myc that are regulated during myeloid differentiation were examined (FIG. 1D). Consistent with monocytic differentiation, the expression of the monocytic transcription factor CEBP/β was upregulated almost 10-fold compared with vehicle-treated cells at 5 days after treatment with 6BT. Also supportive of the induction of myeloid differentiation, the expression of the proliferation-related transcription factor c-myc is rapidly down-regulated after 6BT treatment.

6BT Induced Terminal Differentiation

To assess the ability of 6BT to affect leukemic cell growth, its effects on HL-60 cell proliferation were measured. 6BT led to a significant inhibition of HL-60 cell growth compared with the vehicle control. At the doses used, 6BT induces even more growth inhibition than ATRA (30%±7.1% versus 58%±6.5% of vehicle-treated cells; FIG. 2A). To determine the mechanism of growth inhibition, cell cycle analysis was performed. 6BT growth inhibition involves accumulation of cells in the $G_0$-$G_1$ phase of the cell cycle with >80% of cells present in $G_0$-$G_1$ compared with 55% in the vehicle control at 72 hours after treatment (FIG. 2B). Consistent with accumulation in the $G_0$-$G_1$ phase, 6BT induces p21 that plays a critical role in preventing the $G_1$ to S transition by inhibiting the cyclinD—cyclin-dependent kinase 4/6 complex and down-regulates bcl-2 that among other functions is involved in leukemic cell proliferation (FIG. 2C). To assess whether the observed 6BT-mediated growth inhibition and differentiation results in terminal differentiation, colony forming assays were performed in soft agar. Limited exposure (72 hours) of HL-60 cells to 6BT at doses of 5 and 10 μmol/L almost completely prevented colony growth in soft agar, demonstrating that terminal differentiation can be induced at low noncytotoxic concentrations (FIG. 2D).

Figure 3A:
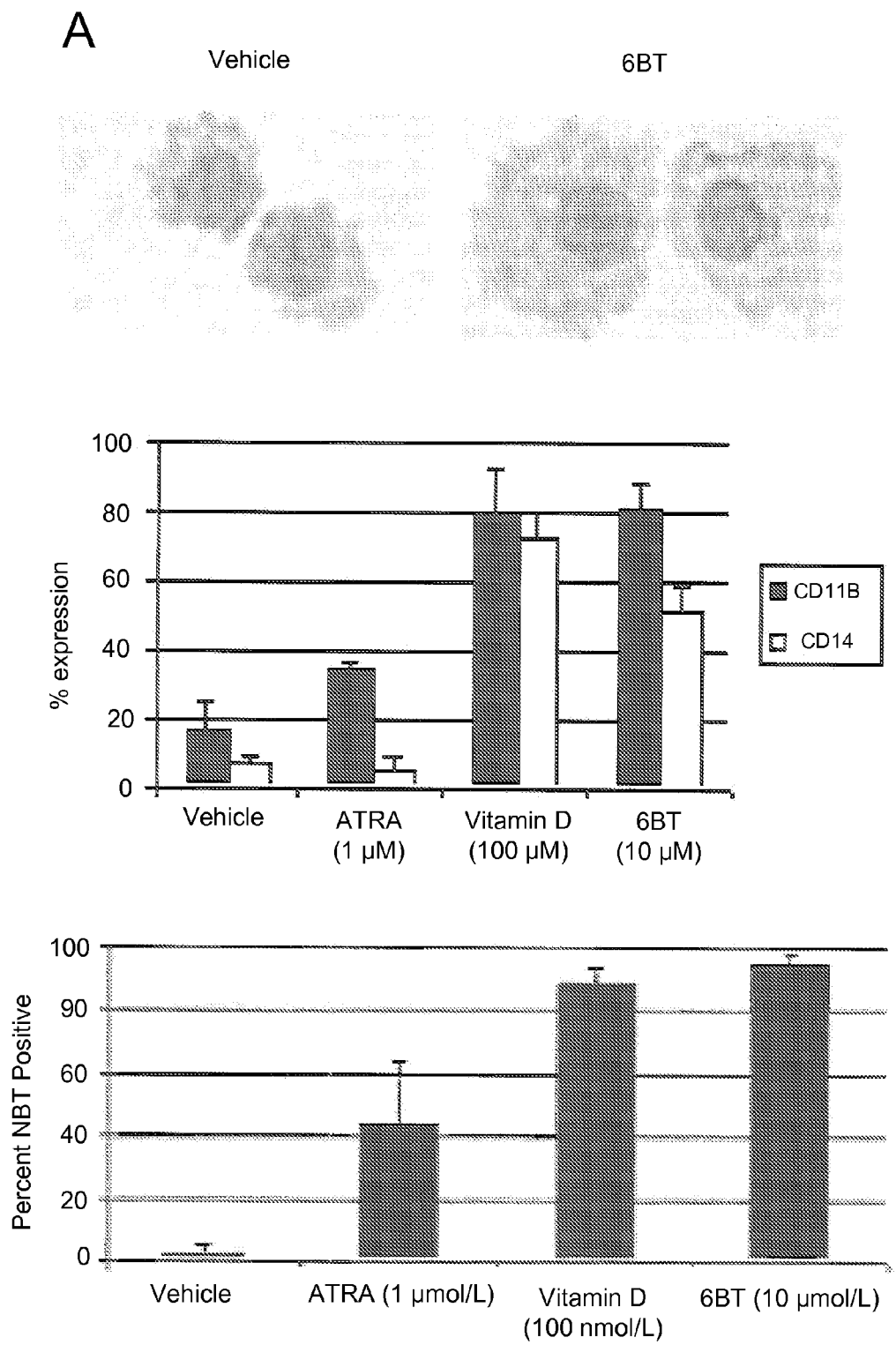
FIG. 3 illustrates 6BT has differentiation and specific cell death activity in multiple AML cell lines and patient samples, and can synergize with clinically used therapeutics. A, 6BT induces monocytic differentiation of OCI-AML3 cells. Cells were treated with 6BT for 4 d and assessed for differentiation by morphology, immunophenotyping, and NBT reduction as described in FIG. 1. B, 6BT can induce differentiation or cell death in primary patient samples. Primary leukemic blasts were purified by flow sorting after staining with CD34-PE. Cells were treated with 6BT (10 μmol/L) for up to 10 d and assessed for differentiation by morphology and NBT reduction and cell death by trypan blue dye exclusion as described in FIG. 1. An exception is that the photograph of the primary AML-M4 patient sample was unstained and taken directly from the tissue culture plate. C, 6BT can synergize in HL-60 cells with ATRA, decitabine, and cytarabine. To assess ATRA and decitabine synergy, HL-60 cells were treated with the indicated compounds for 4 d, and the NBT reduction assay was performed as described in FIG. 1. Results are representative of three independent experiments. To assess cytarabine synergy, cells were treated with the indicated compounds for 72 h and viable cells were assessed by trypan blue staining. Results are an average of three independent experiments. Cyt, cytarabine; dox, doxorubicin.
Figure 3C:
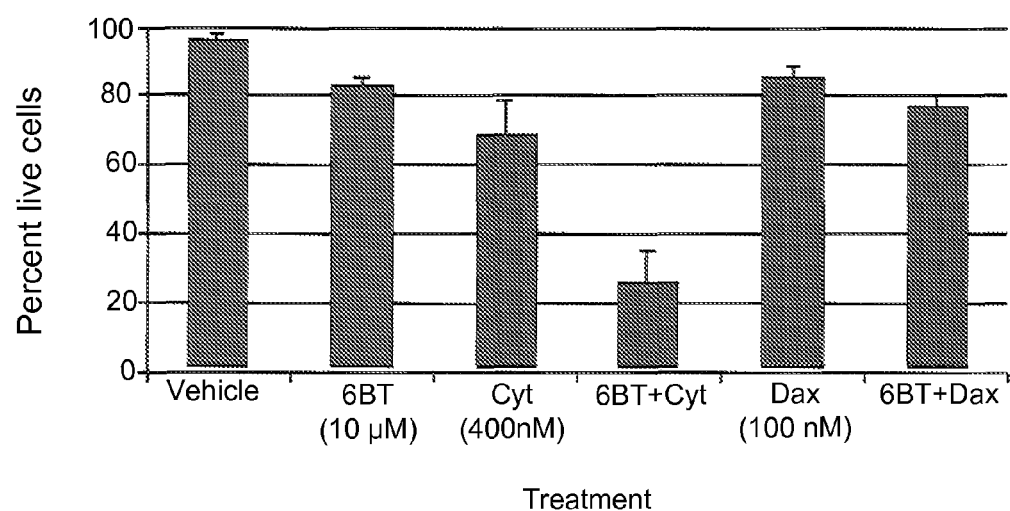

6BT Induced Differentiation or Cell Death in Multiple Leukemic Cell Lines and Primary Patient Samples In addition to HL-60 cells (AML-M2), we assessed the ability of 6BT to induce myeloid differentiation in leukemic cells representing different AML subtypes including OCI-AML3 (AML-M4), HNT34 (AML-M4), MV-411 (AML-M5), and OCIM2 (AML-M6) cells as well as several primary leukemic patient samples. Similar to HL-60 cells, OCI-AML3 cells underwent monocyte/macrophage differentiation in response to 6BT as measured by morphology, NBT reduction, and immunophenotyping (FIG. 3A). Both CD11b and CD14 were significantly up-regulated in OCI-AML3 cells, suggesting monocytic differentiation. In contrast, ATRA treatment leads to granulocytic differentiation and only up-regulates CD11b, whereas Vitamin D3 also leads to monocytic differentiation.

Surprisingly, in contrast to OCI-AML3 cells, both HNT34 and MV-411 cells undergo cell death to low concentrations of 6BT with an $LD_{50}$ at 5 days of 0.5 and 2 μmol/L for these cell lines, respectively. In contrast, the $LD_{50}$ at 5 days for OCIAML3 and HL-60 cells is >100 and 30 μmol/L, respectively. Subtoxic concentrations of 6BT do not induce evidence of differentiation in HNT34 or MV-411 cells (data not shown). The OCIM2 cells did not respond to up to 30 μmol/L of 6BT by differentiation or cell death (data not shown). Besides leukemic cell lines, 6BT can also induce myeloid differentiation and, in some cases, cell death of primary leukemic patient samples. Of five leukemic samples tested, two showed evidence of differentiation (AML-M4 and chronic myelogenous leukemia), two different patient samples showed 6BT-mediated cell death (AML-M2 and AML-M4), and one sample seemed nonresponsive (AML-M5; FIG. 3B). One of the two patient samples that exhibited 6BT-mediated differentiation is from a patient with the closely related myeloid disorder, chronic myeloid leukemia in blast crisis, indicating the possible utility of 6BT in this disease as well. The other patient sample is derived from a patient with AML-M4 with relapsed leukemia. This patient sample leed to dramatic morphologic changes characterized by attachment of the vast majority of leukemic cells to the tissue culture plate as well as an increase in NBT reduction activity (FIG. 3B). Both patient samples that exhibited cell death showed >90% dead cells as shown by morphology and trypan blue dye exclusion after 6BT treatment (FIG. 3B).

As 6BT induced differentiation activity and/or cell death against leukemic cell lines and patient samples at low micromolar concentrations, the potential toxicity of 6BT against nonmalignant cell types was assessed. Of particular note, the $LD_{50}$ of 6BT on normal human bone marrow cells is >100 μmol/L, which was the highest dose tested. Similarly, the $LD_{50}$ was >100 μmol/L for the other cell types examined including human umbilical vein endothelial cells, mouse embryonic fibroblasts, and human mononuclear cells.

6BT Synergized with Other Chemotherapy Agents in Treating Leukemic Cells

We also investigated if 6BT has synergistic effects on leukemic cells in combination with agents that had been clinically used in the treatment of AML. 6BT synergized with decitabine (a hypomethylating agent used for myelodysplastic syndrome and AML) and low doses of ATRA to induce differentiation, indicating these compounds likely worked through different pathways (FIG. 3D). Co-treatment of HL-60 cells with a low dose of 6BT (1 μmol/L) led to an increase in NBT reduction from 20% with 6BT alone to 77% with decitabine (100 ng/mL) and 89% with ATRA (250 nmol/L).

In addition, 6BT was tested for its ability to enhance cytarabine-mediated cell death. The currently used AML chemotherapeutic, cytarabine, is a nucleoside analogue known to primarily use the ent1 nucleoside transporter to enter and exit cells. As 6BT is a potent ent1 inhibitor, the ability of 6BT to inhibit or synergize with cytarabine-mediated leukemia cell killing was assessed. 6BT was found to significantly augment cytarabine-mediated HL-60 cell death. After 48 hours of treatment with cytarbine alone (400 nmol/L), 68.8%±9.9% of cells were alive compared with only 26.6%±8.8% after co-treatment with 6BT. Another chemotherapeutic, doxorubicin, which does not depend upon ent1, did not show synergy with 6BT (FIG. 3D). This result revealed the potential that ent1 may be a desirable drug target for combination therapies with cytarabine or other nucleoside analogues that primarily use ent1.

6BT Showed High Activity in Mouse Xenograft Experiments

Mouse AML xenograft models were used to determine the in vivo activity of 6BT. First, 6BT was assessed for its ability to inhibit the growth of established HL-60 s.c. tumors in nude mice. In the established tumor model, tumors were significantly smaller after 6BT treatment (150 mg/kg) compared with vehicle-treated mice F5 (0.16 grams±0.05 grams versus 0.73 grams±0.28 grams; FIG. 4A-B).

Flow cytometric analysis of the dissected tumors (n=3) at the end of the study period shows evidence of the induction of the mature myeloid marker CD11b (27.7%±1.5% in the vehicle and 63.3%±6.4% in the 6BT-treated tumors). Surprisingly, there was no difference in CD14 expression between the tumors in the 6BT and vehicle mice.

Figure 4C:
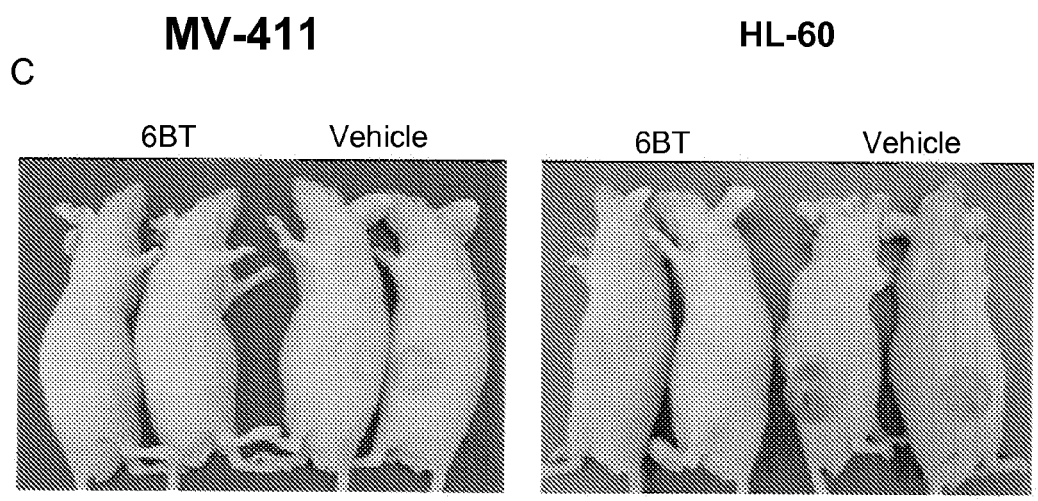
FIG. 4 illustrates 6BT has in vivo activity in both tumor progression and tumor formation models. A, 6BT inhibits HL-60 cell tumor progression. Representative picture of the mice and dissected tumors at the end of the study period. B, 6BT-treated mice exhibit significantly smaller tumors in the tumor progression model. Results shown represent the average weight of tumors dissected from the mice at the end of the study period. C, 6BT completely prevents MV4-11 and HL-60 tumor formation. Representative pictures are shown after the mice were sacrificed at 4 wk after tumor cell inoculation.

In the second model system, the ability of 6BT to prevent either HL-60 or MV-411 tumor formation in nude mice was assessed. In this model, 6BT treatment initiated 1 day after leukemic cell inoculation completely prevented tumor formation of both leukemic cell types in all five mice tested for each cell line with bilateral tumor cell inoculations (FIG. 4C). Therefore, as a single agent, 6BT exhibits in vivo activity.

Phosphorylation of 6BT was Required for Differentiation Induction

To begin to elucidate the mechanism of 6BT-mediated differentiation induction, a closely related compound 6-methylthioinosine (6MT) was used as a model. 6BT is nearly identical in chemical structure to 6MT except for substitution of a methyl group for the benzyl group. As 6MT is monophosphorylated by adenosine kinase, the role of phosphorylation in 6BT activity was assessed. Phosphorylation of 6BT is required for its differentiation activity as there is complete loss of 6BT-mediated differentiation induction of HL-60 cells with coincubation of 1 nmol/L of the specific adenosine kinase inhibitor, 5-iodotubericin (FIG. 5A). The requirement of 6BT phosphorylation for its activity also provides strong evidence that it enters leukemic cells.

6BT Depletes ATP Stores in HL-60 Cells

Because monophosphorylated 6MT is known to act as a potent inhibitor of the enzyme amidophosphoribosyltransferase, the first committed step in de novo purine synthesis, the ability of 6BT to deplete ATP, was assessed. 6BT was found to potently deplete ATP stores in HL-60 cells (FIG. 5B). Treatment of HL-60 cells with 6BT (5 µmol/L) leads to rapid depletion of ~70% of ATP stores within 24 hours. The depletion of ATP is not due to the differentiation process itself as, after 6BT treatment, HL-60 cells contain 30.3%±9.2% of the ATP levels of vehicle-treated cells compared with 93.0%±9.1% in ATRA-treated cells (1 µmol/L). Although 6BT does induce growth arrest of HL-60 cells and the cells ultimately die, the time course of significant cell death (about 7 days) and ATP depletion (hours) is significantly different. 6BT was also found to deplete ATP in OCI-AML3 cells (50-60% at 24 hours) but did not lead to significant ATP depletion, at least at early time points, in MV411 cells that undergo 6BT-mediated cell death instead of differentiation. Due to the induction of cell death in MV411 cells, it was not possible to assess the ATP depletion at 24 hours.

6BT used a Nonent1 Transporter to Enter Leukemic Cells

Figure 5C:
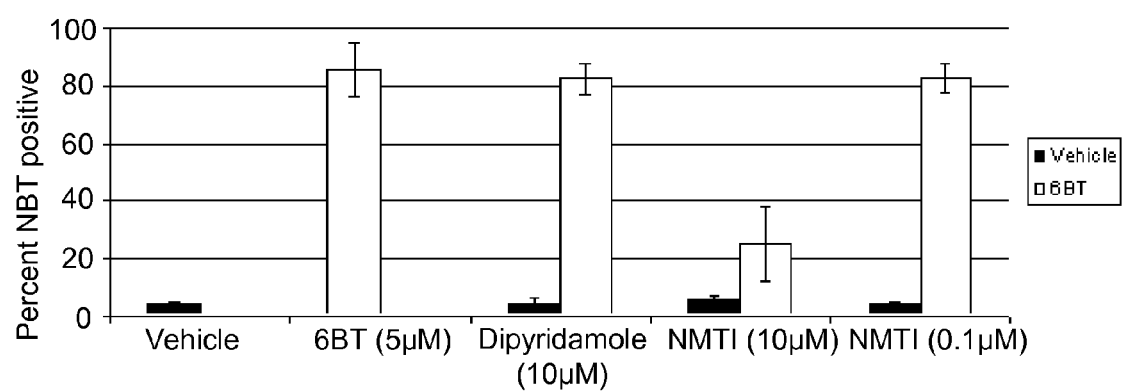
FIG. 5 illustrates the mechanism by which 6BT can induce differentiation. A, phosphorylation of 6BT is essential for its activity. HL-60 cells were treated with 6BT alone or in combination with the specific adenosine kinase inhibitor, 5 iodotubericidin for 4 d, and the NBT reduction assay was performed as described in FIG. 1. Results are an average of three independent experiments. B, 6BT potently depletes ATP stores in leukemic cells. HL-60, OCI-AML3, and MV411 cells were treated for the indicated time points with 6BT, ATRA, or vehicle. An equal number of viable (as measured by trypan blue) cells was assessed for ATP using a luciferase-based assay system. The results shown represent the amount of ATP in the treated groups as a percentage of the ATP present in the vehicle-treated group. Results are an average of three independent experiments. C, inhibition of ent1 does not block 6BT-mediated uptake into leukemic cells. HL-60 cells were treated with the indicated compounds with or without a low dose of 6BT (5 µmol/L) for 3 d, and the NBT reduction assay was performed as detailed in FIG. 1. Results are an average of three independent experiments.
Figure 6:
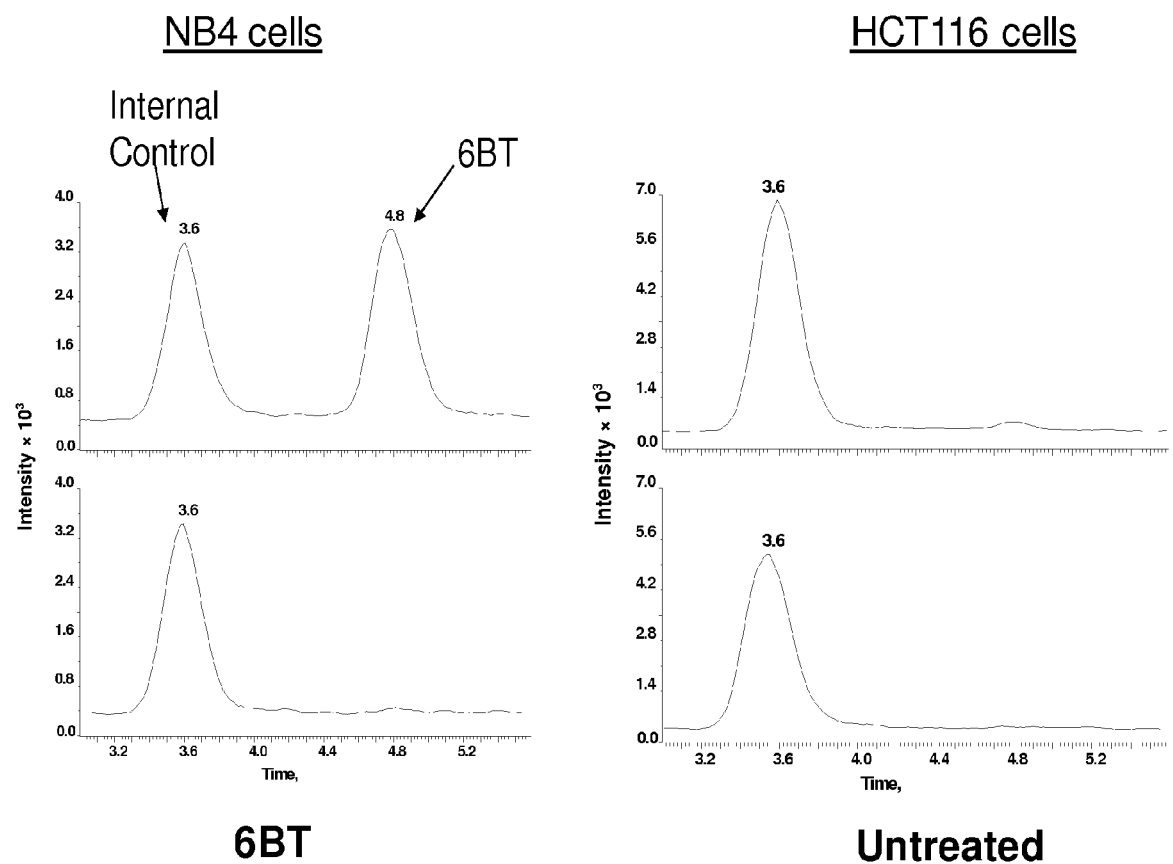
FIG. 6 illustrates plots showing the preferential uptake of 6BT after 24 hours of treatment of NB4 cells (leukemia cells) or HCT116 cells (colon cancer cells) by HPLC.

To begin to elucidate how 6BT may enter leukemic cells, well characterized nucleoside transporter inhibitors were used. Neither nitrobenzylthioinsoine (NBTI) nor dipyridamole was able to block low-dose 6BT-mediated differentiation of HL-60 cells at optimal doses for the inhibition of ent1 (FIG. 5C). In contrast, when NBTI was used at an extremely high concentration (10 µmol/L) that is capable of inhibiting several other nucleoside transporters, a dramatic decrease in 6BT-mediated differentiation was observed (86%±9.6%–25%±13.20%). Therefore, 6BT is likely capable of entering leukemic cells through a nonent1—mediated pathway that is at least partially inhibited by NBTI. It is well-established that leukemic cells can express nucleoside transporters not widely expressed on other cells.

Materials and Methods

Chemicals 1,25 dihydroxyvitamin D3, ATRA, Nitroblue tetrazolium (NBT), Nitrobenzylthioinosine, iodotubericin, and phorbol 12-myristate 13-acetate (PMA) were purchased from Sigma. 6BT was kindly provided by the National Cancer Institute (NCI) Developmental Therapeutics Program.

Cell Lines

HL-60 and MV-411 cells were obtained from American Type Culture Collection. OCI-AML3, HNT-34, and OCIM2 cells were obtained from DSMZ. Patient samples were obtained from the stem cell core facility at University Hospitals Case Medical Center. MEF and human umbilical vascular endothelial cells (HUVEC) were kindly provided from the laboratory of Dr. Mary Laughlin. Cells were cultured in Iscove's modified Dulbecco's medium (Invitrogen) except for MEF (DMEM; Invitrogen) and HUVEC (EGM Lonza). Medium was supplemented with 10% fetal bovine serum (FBS; Invitrogen), penicillin G (100 µg/mL), and streptomycin (100 µg/mL). Mononuclear cells were separated by Ficoll-Hypaque (Sigma) density-gradient centrifugation, and for selected patients, leukemic myeloblasts were isolated by flow sorting after staining with anti-CD34 PE (Becton Dickinson).

Cell Proliferation and Viability

Cell proliferation was assessed by manual counting cells with a hematocytometer. Cell viability was assessed by the trypan blue dye exclusion method.

Compound Library Screen

For screening, 100 µL of HL-60 cells ($5 \times 10^5$ cells/mL) were cultured in 96-well plates. Cells were treated with 10 µmol/L of compounds from the following libraries: Lopac (Sigma), Prestwick (Prestwick Chemical), and NCI diversity collection. DMSO (0.1%) and ATRA (1 µmol/L) were used as negative and positive controls, respectively. After 5 d, the differentiation of the cells was assessed by the NBT reduction assay. To perform the NBT assay, 20 µL of a solution of NBT (5 mg/mL) and PMA 100 ng/mL (as a stimulant of the respiratory burst) were added to the HL-60 cells. The cells were incubated at 37° C. for 30 min and the color of the wells was assessed. Those wells that displayed a visual color change from the production of blue insoluble formazan greater than the negative control were examined microscopically to determine the percentage of blue cells. At least 200 cells were counted for each positive well.

Differentiation

NBT reduction was performed in a similar manner as described for the compound library screen Immunophenotyping was performed by co-staining cells with CD11b-PE and CD14-FITC (Becton Dickinson). The stained samples were run on a Beckman Coulter Cytomics FC 500 cytometer. For morphology assessment, cytospin preparations were made using a Shandon cytospin3 cytocentrifuge, and the slides were stained with a modified wright-giemsa stain.

Soft Agar Clonogenic Assay

HL-60 cells ($2 \times 10^5$ cells/mL) were treated with 6BT or vehicle for 3 d. The cells were washed twice with PBS, and 3,000 cells were dissolved in 3 mL of 0.35% Soft Agar (Noble Agar; Sigma) supplemented with 20% FBS. The cells were incubated for 10 d in 37° C. in a 5% $CO_2$ incubator. After 10 d, the colonies were counted under a light microscope.

Cell Cycle Analysis

HL-60 cells were treated with 6BT or vehicle for 3 d. Cells were fixed overnight at −20° C. in methanol. Cells were washed in PBS, treated with RNase A (final concentration, 0.5 µg/mL; Sigma), and stained with propidium iodide (50 µg/mL). The cells were kept at 4° C. for 30 to 60 min and analyzed by flow cytometry.

Real-Time PCR

Total RNA was isolated from HL-60 cells treated with 6BT or vehicle at indicated time points, using TRIzol reagent (Invitrogen). RNA was transcribed into cDNA using the Enhanced Avian RT First Strand Synthesis kit (Sigma). Relative quantitative PCR was performed in triplicate using the FastStart SYBR Green Master (Roche Diagnostics) on an Applied Biosystems 7500 Fast Real-TimePCR System. The primers used were CEBP/β5' primer, 5'-GAACAGCAAC-GAGTACCGGGTG-3' (SEQ ID NO: 1), and 3' primer, 5'-CCCATGGCCTTGACCAAGGAG-3' (SEQ ID NO: 2); β-actin 5'primer, 5'-GGACTTCGAGCAAGAGATGG-3' (SEQ ID NO: 3), and 3'primer, 5'-AGCACTGTGTTGGCG-TACAG-3' (SEQ ID NO: 4); c-myc 5' primer, 5'-GC-CACGTCTCCACACATCAG-3' (SEQ ID NO: 5), and 3' primer, 5'-TCTTGGCAGCAGGATAGTCCTT-3' (SEQ ID NO: 6). Thermal conditions of the system were as follows: 95° C. for 5 min, 40 cycles at 95° C. for 15 s, 55° C. for 45 s, and 72° C. for 1 min.

Western Blot Analysis

Western blot analysis was performed with p21 (Cell Signaling), bcl-2 (Santa Cruz biotechnology), and β-actin antibodies (Sigma). Cells were treated with 6BT or vehicle for the indicated times and washed in PBS. Cells were centrifuged and lysed with a Triton containing lysis buffer. Protein lysates (80 μg per lane) were electrophoresed on 10% SDS-polyacrylamide gels and then transferred to polyvinylidene difluoride membranes (Millipore) using a semidry transfer apparatus (Bio-Rad). The membranes were blocked, incubated with the indicated primary antibodies at 4° C. overnight, and then the appropriate horseradish peroxidase—conjugated secondary antibody. Protein bands were visualized by autoradiography after incubation with enhanced chemiluminescence reagent (Pierce).

Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

Having described the invention, the following is claimed:

1. A method of treating acute myeloid leukemia in a subject, the method comprising:
   administering to the subject with acute myeloid leukemia a therapeutically effective amount of at least one inosine analog having the following general formula (I):

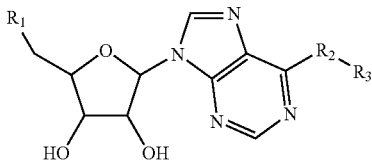

where $R_1$ is OH, monophosphate ($H_2O_3PO-$ or ($O_3PO-)^{2-}$), diphosphate ($H_3(O_3PO)_2-$ or (($O_3PO)_2-)^{3-}$), triphosphate ($H_4(O_3PO)_3-$, (($O_3PO)_3-)^{4-}$), or $OR_a$, where $R_a$ comprises at least one of a straight chain, branched or cyclic alkyl, CO-alkyl, CO-aryl, CO-alkoxyalkyl, arylsulfonyl, aralkylsulfonyl, amino acid residue, fatty acid residue, or a mono, di, or triphosphate thereof;

where $R_2$ is S or O; and where $R_3$ is selected from the group consisting of optionally substituted $C_1$-$C_8$-alkyl; optionally substituted $C_1$-$C_8$-alkenyl; optionally substituted $C_1$-$C_8$-alkynyl; optionally substituted $C_3$-$C_8$-cycloalkyl or $C_3$-$C_8$-cycloalkyl containing 1 or 2 heteroatoms selected from S, O or N in the ring; and optionally substituted phenyl, benzyl, aryl, or heteroaryl;

and combinations thereof; or a pharmaceutically acceptable salt thereof, wherein the inosine analog promotes differentiation of a myeloid leukemia cell.

2. The method claim 1, wherein the inosine analog has the following formula (II):

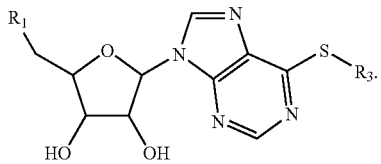

3. The method of claim 2, $R_3$ can be selected from the group consisting of an optionally substituted $C_1$-$C_6$-alkyl, alkenyl, phenyl, benzyl, and aryl.

4. The method of claim 1, wherein inosine analog has the following formula (III):

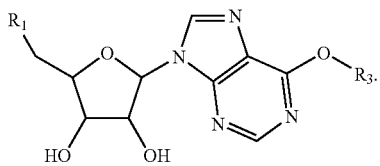

5. The method of claim 4, wherein $R_3$ is selected from the group consisting of an optionally substituted-$C_1$-$C_6$-alkyl, alkenyl, phenyl, benzyl, and aryl.

6. The method of claim 1, wherein the inosine analog has the following formula (IV):

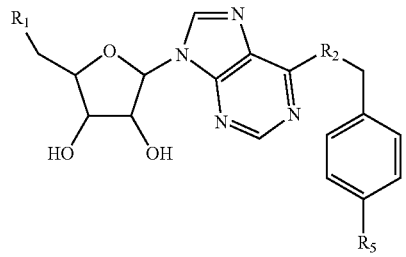

where $R_1$ is OH, monophosphate ($H_2O_3PO-$ or ($O_3PO-)^{2-}$), diphosphate ($H_3(O_3PO)_2-$ or (($O_3PO)_2-)^{3-}$), triphosphate ($H_4(O_3PO)_3-$, (($O_3PO)_3-)^{4-}$), or $OR_a$, where $R_a$ comprises at least one of a straight chain, branched or cyclic alkyl, CO-alkyl, CO-aryl, CO-alkoxyalkyl, arylsulfonyl, aralkylsulfonyl, amino acid residue, fatty acid residue, or a mono, di, or triphosphate thereof;

where $R_2$ is S or O; and where $R_5$ is a hydrogen, halo, fluoro, alkyl, alkyloxy, nitro, cyano, amino, substituted alkyl, aryl or substituted aryl.

7. The method of claim 1, the inosine analog has the following formula (V),

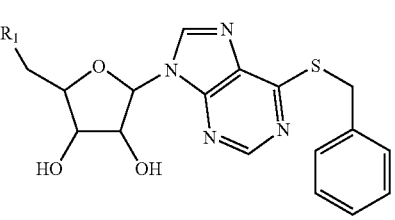

where $R_1$ is OH, monophosphate ($H_2O_3PO-$ or ($O_3PO-)^{2-}$), diphosphate ($H_3(O_3PO)_2-$ or (($O_3PO)_2-)^{3-}$), triphosphate ($H_4(O_3PO)_3-$, (($O_3PO)_3-)^{4-}$), or $OR_a$, where $R_a$ comprises at least one of a straight chain, branched or cyclic alkyl, CO-alkyl, CO-aryl, CO-alkoxyalkyl, arylsulfonyl, aralkylsulfonyl, amino acid residue, fatty acid residue, or a mono, di, or triphosphate thereof.

8. The method of claim 1, further comprising:
   administering an anti-proliferative agent in combination with the inosine analog.

9. The method of claim 8, wherein the anti-proliferative agent is an anti-metabolite and/or a nucleoside analog.

10. A method of treating acute myeloid leukemia in a subject, the method comprising:
    administering to the subject a therapeutically effective amount of at least one anti-proliferative agent and at least one inosine analog having the following general formula (I):

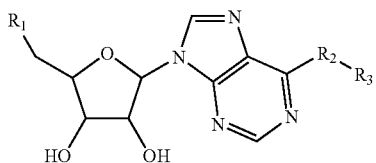

where $R_1$ is OH, monophosphate ($H_2O_3PO-$ or ($O_3PO-)^{2-}$), diphosphate ($H_3(O_3PO)_2-$ or (($O_3PO)_2-)^{3-}$), triphosphate ($H_4(O_3PO)_3-$, (($O_3PO)_3-)^{4-}$), or $OR_a$, where $R_a$ comprises at least one of a straight chain, branched or cyclic alkyl, CO-alkyl, CO-aryl, CO-alkoxyalkyl, arylsulfonyl, aralkylsulfonyl, amino acid residue, fatty acid residue, or a mono, di, or triphosphate thereof;

where $R_2$ is S or O; and where $R_3$ is selected from the group consisting of optionally substituted $C_1$-$C_8$-alkyl; optionally substituted $C_1$-$C_8$-alkenyl; optionally substituted $C_1$-$C_8$-alkynyl; optionally substituted $C_3$-$C_8$-cycloalkyl or $C_3$-$C_8$-cycloalkyl containing 1 or 2 heteroatoms selected from S, O or N in the ring; and optionally substituted phenyl, benzyl, aryl, or heteroaryl;

and combinations thereof; or a pharmaceutically acceptable salt thereof, wherein the inosine analog promotes differentiation of an acute myeloid leukemia cell.

11. The method claim 10, wherein the inosine analog has the following formula (II):

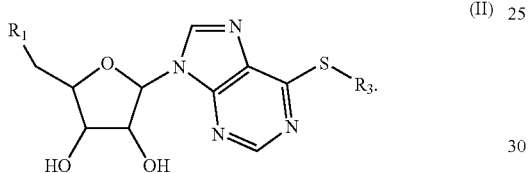

(II)

12. The method of claim 10, $R_3$ can be selected from the group consisting of an optionally substituted $C_1$-$C_6$-alkyl, alkenyl, phenyl, benzyl, and aryl.

13. The method of claim 10, wherein inosine analog has the following formula (III):

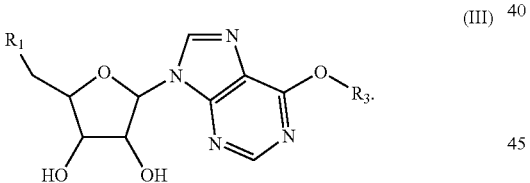

(III)

14. The method of claim 13, wherein $R_3$ is selected from the group consisting of an $C_1$-$C_6$-alkyl, alkenyl, phenyl, benzyl, and aryl.

15. The method of claim 10, wherein the inosine analog has the following formula (IV):

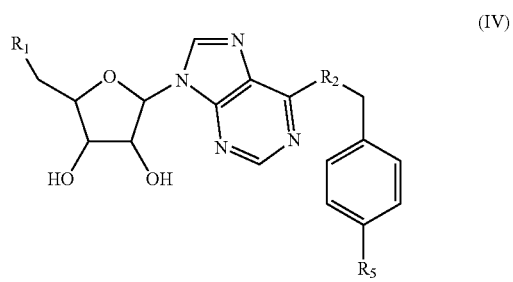

(IV)

where $R_1$ is OH, monophosphate ($H_2O_3PO-$ or ($O_3PO-)^{2-}$), diphosphate ($H_3(O_3PO)_2-$ or (($O_3PO)_2-)^{3-}$), triphosphate ($H_4(O_3PO)_3-$, (($O_3PO)_3-)^{4-}$), or $OR_a$, where $R_a$ comprises at least one of a straight chain, branched or cyclic alkyl, CO-alkyl, CO-aryl, CO-alkoxyalkyl, arylsulfonyl, aralkylsulfonyl, amino acid residue, fatty acid residue, or a mono, di, or triphosphate thereof;

where $R_2$ is S or O; and where $R_5$ is a hydrogen, halo, fluoro, alkyl, alkyloxy, nitro, cyano, amino, substituted alkyl, aryl or substituted aryl.

16. The method of claim 10, the inosine analog has the following formula (V),

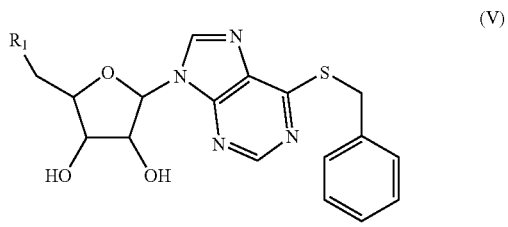

(V)

where $R_1$ is OH, monophosphate ($H_2O_3PO-$ or ($O_3PO-)^{2-}$), diphosphate ($H_3(O_3PO)_2-$ or (($O_3PO)_2-)^{3-}$), triphosphate ($H_4(O_3PO)_3-$, (($O_3PO)_3-)^{4-}$), or $OR_a$, where $R_a$ comprises at least one of a straight chain, branched or cyclic alkyl, CO-alkyl, CO-aryl, CO-alkoxyalkyl, arylsulfonyl, aralkylsulfonyl, amino acid residue, fatty acid residue, or a mono, di, or triphosphate thereof.

17. The method of claim 10, wherein the anti-proliferative agent is an anti-metabolite and/or a nucleoside analog.

* * * * *

SEQUENCE LISTING

<160> NUMBER OF SEQ ID NOS: 6

<210> SEQ ID NO 1
<211> LENGTH: 22
<212> TYPE: DNA
<213> ORGANISM: Homo sapiens

<400> SEQUENCE: 1
gaacagcaac gagtaccggg tg                                              22

<210> SEQ ID NO 2
<211> LENGTH: 21
<212> TYPE: DNA
<213> ORGANISM: Homo sapiens

<400> SEQUENCE: 2
cccatggcct tgaccaagga g                                               21

<210> SEQ ID NO 3
<211> LENGTH: 20
<212> TYPE: DNA
<213> ORGANISM: Homo sapiens

<400> SEQUENCE: 3
ggacttcgag caagagatgg                                                 20

<210> SEQ ID NO 4
<211> LENGTH: 20
<212> TYPE: DNA
<213> ORGANISM: Homo sapiens

<400> SEQUENCE: 4
agcactgtgt tggcgtacag                                                 20

<210> SEQ ID NO 5
<211> LENGTH: 20
<212> TYPE: DNA
<213> ORGANISM: Homo sapiens

<400> SEQUENCE: 5
gccacgtctc cacacatcag                                                 20

<210> SEQ ID NO 6
<211> LENGTH: 22
<212> TYPE: DNA
<213> ORGANISM: Homo sapiens

<400> SEQUENCE: 6
tcttggcagc aggatagtcc tt                                              22